United States Patent
Berg et al.

(10) Patent No.: US 12,201,110 B2
(45) Date of Patent: Jan. 21, 2025

(54) POLYMERIC PARTICLES CONTAINING MICROORGANISMS

(71) Applicants: Technische Universität Graz, Graz (AT); Biotenzz Gessellschaft für Biotechnologie mbH, Graz (AT)

(72) Inventors: Gabriele Berg, Graz (AT); Henry Müller, Graz (AT)

(73) Assignees: TECHNISCHE UNIVERSITÄT GRAZ, Graz (AT); BIOTENZZ GESELLSCHAFT FÜR BIOTECHNOLOGIE MBH, Graz (AT)

( * ) Notice: Subject to any disclaimer, the term of this patent is extended or adjusted under 35 U.S.C. 154(b) by 0 days.

(21) Appl. No.: 18/113,384

(22) Filed: Feb. 23, 2023

(65) Prior Publication Data

US 2023/0189799 A1 Jun. 22, 2023

Related U.S. Application Data

(62) Division of application No. 16/648,535, filed as application No. PCT/EP2018/075760 on Sep. 24, 2018, now Pat. No. 11,589,579.

(30) Foreign Application Priority Data

Sep. 22, 2017 (WO) ................. PCT/EP2017/073994

(51) Int. Cl.
| | | |
|---|---|---|
| *A01N 25/28* | (2006.01) |
| *A01N 63/20* | (2020.01) |
| *A01N 63/22* | (2020.01) |
| *A01N 63/27* | (2020.01) |
| *A01N 63/30* | (2020.01) |
| *A61K 9/16* | (2006.01) |
| *A61K 35/74* | (2015.01) |
| *C12N 1/04* | (2006.01) |
| *C12N 1/20* | (2006.01) |

(52) U.S. Cl.
CPC ............. *A01N 25/28* (2013.01); *A01N 63/20* (2020.01); *A01N 63/22* (2020.01); *A01N 63/27* (2020.01); *A01N 63/30* (2020.01); *A61K 9/1617* (2013.01); *A61K 9/1652* (2013.01); *A61K 35/74* (2013.01); *C12N 1/04* (2013.01); *C12N 1/20* (2013.01)

(58) Field of Classification Search
CPC ........ A01N 25/28; A01N 63/20; A01N 63/30; A61K 9/1617; A61K 9/1652; A61K 35/74; C12N 1/04
See application file for complete search history.

(56) References Cited

U.S. PATENT DOCUMENTS

| | | | | |
|---|---|---|---|---|
| 2012/0135017 A1* | 5/2012 | Harel | ..................... | A61K 47/38 |
| | | | | 435/235.1 |
| 2016/0002588 A1* | 1/2016 | Zhang | ................... | C12N 11/04 |
| | | | | 435/252.4 |

OTHER PUBLICATIONS

Kragh et al, Role of multicellular aggregates in biofilm formation, American society for microbiology, vol. 7, issue 2, Mar./Apr. 2016 (Year: 2016).*
Rathore et al (Microencapsulation of microbial cells), Journal of Food Engineering, 116 (2013) 369-381. (Year: 2013).*

* cited by examiner

*Primary Examiner* — Mina Haghighatian
(74) *Attorney, Agent, or Firm* — LOZA & LOZA, LLP; Michael Fedrick

(57) ABSTRACT

The present invention relates to polymeric particles comprising a biodegradable polymer, and at least one microorganism in a total concentration of at least $10^8$ CFU/g dry weight that is stable for at least 35 weeks at 30° C. and optionally additional carriers and additives as well as to methods for producing polymeric particles and use thereof.

11 Claims, 16 Drawing Sheets

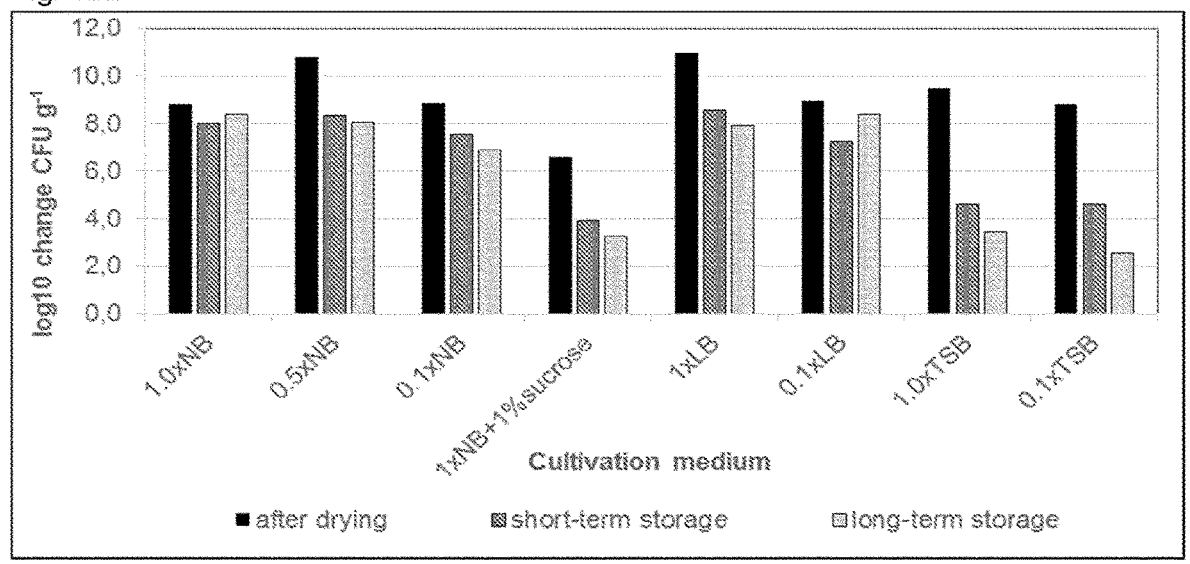

POLYMERIC PARTICLES CONTAINING MICROORGANISMS

CROSS-REFERENCE TO RELATED APPLICATIONS

This application is a divisional of U.S. patent application Ser. No. 16/648,535, filed on Mar. 18, 2020 and entitled POLYMERIC PARTICLES CONTAINING MICROORGANISMS, which is the U.S. national stage of International Patent Application No. PCT/EP2018/075760 filed on Sep. 24, 2018, which claims the benefit of priority from International Patent Application PCT/EP2017/073994 filed on Sep. 22, 2017. The disclosures of the foregoing applications are incorporated herein by reference in their entirety.

FIELD OF THE INVENTION

The present invention relates to immobilization and cultivation methods inducing metabolic traits of long-term survival for improving the viability of microorganisms during storage and application and viable and stable microbial compositions.

BACKGROUND ART

The application of microorganisms for plant protection, growth promotion and fertilization purposes at commercial scale strongly depends on the reliability of microbial preparations. Particularly, when microbial agents are intended to be applied as additive in coatings for seed treatment processes, the requirements for the formulation are high. Apart from the general desiccation stress in dry formulations, microorganisms are additionally exposed to physical (e.g. shear forces), thermal as well as to detrimental chemicals (e.g., pesticidal agents). Except for some spore-forming bacteria, the majority of microorganisms are unable to cope with those stress moments and lose viability. To circumvent problems with the stability of microbial strains, mostly Gram-positive bacteria with spore-forming ability are currently being commercialized. Notwithstanding, sensitive Gram-negative bacteria possess a greater potential for biological plant protection and fertilization.

Bashan et al. (*Appl Environ Microbiolv.*51 (5); 1986) describe a method of inoculation of non-symbiotic rhizosphere bacteria in biodegradable polymeric substances. *Azospirillum brasilense* Cd is grown in nutrient broth to a final concentration of $10^9$ CFU/ml. The bacterial cells were then entrapped in alginate beads. After washing, the beads were again incubated to allow bacteria multiplication inside the beads. After washing, the beads were either kept at 4° C. in hermetically sealed flasks under moist conditions or as lyophilized beads.

Alginate is considered as the most common biomaterial for the encapsulation of bacterial and/or other type of cells. In presence of multivalent ions, alginate form three-dimensionally structured hydrogels in which bacterial cells are embedded (John R P et al., *Crit Rev Biotechnol.* 2011 September; 31 (3):211-26). Although favoring in some extent the survivability of microbial cells due to the high moisture rate, saturated alginate hydrogels are unsuitable and impractical for use as commercial products. In dried alginate aggregates with low moisture content, however, the vitally of the majority of microorganisms is severely impaired.

Usually, microbial cells are produced by submerged fermentation processes using liquid media. In a dispersed form, cells grow planktonically and possess a metabolism that favors multiplication rates and biomass gain, but reduces the robustness and compromise stress tolerance. Despite the application of protective additives to compensate missing resilience, survival rates are insufficient.

Despite much attention on the stabilization of microorganisms in formulations suitable for large scale applications, including seed treatment processes, no appropriate solution is currently available (Vemmer & Patel, 2013).

SUMMARY OF INVENTION

It is the objective of the present invention to provide for an improved immobilization-based cultivation and formulation method to induce metabolic traits of long-term survival for improving the viability of microorganisms during storage and application.

The object is solved by the subject of the present invention.

According to the invention there are provided polymeric particles comprising a polymer, at least one microorganism in a total concentration of at least $10^9$ CFU/g dry weight and optionally additional carriers and additives, wherein said polymeric particles are dry particles.

According to a further embodiment of the invention there are provided polymeric particles comprising a polymer, at least one microorganisms in a total concentration of at least $10^9$ CFU/g dry weight and optionally additional carriers and additives, wherein said at least one microorganism is comprised as self-organized multicellular aggregate.

According to a further embodiment of the invention there are provided polymeric particles comprising a polymer, at least one microorganisms in a total concentration of at least $10^8$ CFU/g dry weight and optionally additional carriers and additives, wherein said particles have an average diameter of about 500 μm, or less. In some embodiments, the particles have an average diameter of about 200 μm, or less. In some embodiments, the particles have an average diameter of about 100 μm, or less. In some embodiments, the particles have an average diameter of about 75 μm, or less. In some embodiments, the particles have an average diameter of about 50 μm or less. In some embodiments, the particles have an average diameter of about 25 μm or less. In some embodiments, the particles have an average diameter of about 10 m or less. In some embodiments, the particles have an average diameter of about 5 μm or less. In some embodiments, the particles have an average diameter of about 1 μm.

In particular, the microorganisms described herein are bacterial and/or fungal cells.

Specifically, the cells of the microorganisms are encapsulated in the polymer. In some embodiments, the cells of the encapsulated microorganisms comprise bacterial cells of one or more Phyla selected from the group consisting of *Firmicutes* and *Proteobacteria*. In some embodiments, the cells of the encapsulated microorganisms comprise bacterial cells of one or more Classes selected from the group consisting of Betaproteobacteria, Bacilli Alphaproteobacteria, and Gammaproteobacteria. In some embodiments, the cells of the encapsulated microorganisms comprise bacterial cells of one or more Orders selected from the group consisting of Aeremonadales, Baci Hales, Bifidobacteriales, Burkholderiales, Enterobacterales, Lactobacillales, Neisseriales, Oceanospirillales, Pseudomonadales, Rhizobiales, Rhodospirillales, Sphingomonadales, Streptomycetales, and Xanthomonadales. In some embodiments, the cells of the encapsulated microorganisms comprise bacterial cells of one or more Families selected from the group consisting of Aspergillaceae, Bacillaceae, Bilidobacteriaceae, Bradyrhizobiacea, Burkholderiaceae, Chromobacteriaceae, Clavicipitaceae, Cordycipitaceae, Coniothyriaceae, Enterobacteriaceae, Erwiniaceae, Hypocreaceae, Lactobacillaceae, Leuconostocaceae, Methylobacteriaceae, Moraxellaceae, Oceanospirillaceae, Oxalobacteraceae, Paenibacillaceae, Pasteuriaceae, Pseudomonadaceae, Rhizohiaceae, Rhodospirillaceae, Sphingomonadaceae, Sclerotiniaceae, Streptococcaceae, Streptomycetaceae, *Xanthomona daceae*, and Yersiniaceae. In some embodiments, the cells of the encapsulated microorganisms comprise bacterial cells of one or more Genera selected from the group consisting of *Azaspirillum, Azotobacter, Bacillus, Bradyrhizobium, Burkholderia, Ensifer, Enterobacter, Herbaspirillum, Lysobacter, Methylobacterium, Paraburkholderia, Pseudomonas, Rhizobium, Serratia, Sphingomonas*, and *Sienotrophomonas*.

In some embodiments, the cells of the encapsulated microorganisms comprise fungal cells of the Phylum *Ascomycota*. In some embodiments, the cells of the encapsulated microorganisms comprise fungal cells of one or more Classes selected from the group consisting of Dothideomycetes, Eurotiomycetes, Leotiomycetes and Sordariomycetes. In some embodiments, the cells of the encapsulated microorganisms comprise fungal cells of one or more Orders selected from the group consisting of Eurotiales, Helondies, Hypocreales, and Pleosporales. In some embodiments, the cells of the encapsulated microorganisms comprise fungal cells of one or more Families selected from the group consisting of Aspergillaceae, Clavicipitaceae, Clavicipitaceae, Coniothyriaceae, Cordycipitaceae, Hypocreaceae, and Sclerointiaceae. In some embodiments, the cells of the encapsulated microorganisms comprise fungal cells of the Genera selected from the group consisting of *Beauveria, Coniothyrium, Ghocladium, Lecanicillum, Metarhizium, Paecilomyces, Penicillium, Pochonia, Sclerotinia, Trichoderma* and *Verticillium*.

A further embodiment of the invention relates to polymeric particles, wherein the at least two microorganism cells are of different origin, specifically of different strains or species or genus or kingdom.

Specifically, the microorganisms, bacterial and/or fungal cells are comprised as multicellular aggregates thereby embedded in a self-produced extracellular biogenic matrix within the polymeric particle. This multicellular lifestyle supports survival strategies which combine the production of protection molecules and mechanisms as well as the induction of a genetic control system that shifts microorganisms into a dormancy-like state. In one embodiment, the polymeric particles are wet and at least one of the multicellular aggregates is between 14 µm and 43 µm in diameter.

According to a further embodiment of the invention the polymer is a biodegradable polymer. A further embodiment of the invention relates to polymeric particles as described herein, wherein the biodegradable polymer is selected from the group consisting of alginate, agarose, agar, gelatin, polyacrylamide, chitosan, and polyvinyl alcohol.

In some embodiments, the biodegradable polymer is an alginate. In some embodiments, the biodegradable polymer is sodium alginate.

A further embodiment of the invention relates to polymeric particles as described herein, wherein the particles have an average diameter of about 1 to 2,000 µm, or of about 25 to 1,000 µm, or of about 50 to 500 µm, or of about 100 to 250 µm. In some embodiments, particles have an average diameter of about 1 µm, 10 µm, 25 µm, 50 µm, 75 µm, 100 µm, 150 µm, 200 µm, 250 µm, 300 µm, 350 µm, 400 µm, 450 µm, or of about 500 µm.

A further embodiment of the invention relates to polymeric particles as described herein, wherein the viability of the microorganisms is substantially maintained for a storage period of at least 35 weeks at 30° C. and at least 52 weeks at 4° C.

A further embodiment of the invention relates to polymeric particles as described herein, wherein at leak 5, 10, 25, 50, 60, 70, 80, 90, or 95% of the microorganism cells are viable after a storage period of 35 weeks at 30° C.

One embodiment of the invention relates to a method for improving the viability of microorganisms during storage and application, comprising the steps of:
 a) suspending one or more pre-cultures of microorganism cells in a polymeric solution,
 b) immobilizing said microorganism cells by dropping the solution of step a) into multivalent ion solution thereby obtaining polymeric particles,
 c) cultivating the encapsulated microorganisms in said particles for at least 12 h in liquid cultivation media until an increase of the cell density of at least 2 to 10 log is obtained.

One embodiment of the invention relates to a method for improving the viability of microorganisms during storage and application, comprising the steps of:
 a) suspending one or more pre-cultures of microorganism cells to a cell density of about $10^0$-$10^8$ CFL/ml in a polymeric substance solution,
 b) immobilizing said microorganism cells by dropping the solution of step a) into multivalent ion solution thereby obtaining polymeric particles,
 c) cultivating the encapsulated microorganisms in said particles for at least 12 h in liquid cultivation media until cell density of at least about $10^9$ CFU/g dry weight is obtained.

In one embodiment of the invention, each microorganism is pre-cultured individually up to a cell density of about $10^9$-$10^{10}$ CFU/ml. Depending on the microorganism, the pre-culture is suspended in a polymeric substance solution in the method as described herein to a cell density of about $10^0$-$10^8$ CFU/ml. In particular, the cell density in the suspension of pre-culture and polymeric substance solution is about $10^0$, 10, $10^2$, $10^3$, $10^4$, $10^5$, $10^6$, $10^7$, or $10^8$ CFU/ml. In some embodiments, the cell density in the suspension of pre-culture and polymeric substance solution is about $10^0$ to $10^1$ CFU/ml. In some embodiments, the cell density in the suspension of pre-culture and polymeric substance solution is about $10^1$ to $10^2$ CFU/ml. In some embodiments, the cell density in the suspension of pre-culture and polymeric substance solution is about $10^2$ to $10^3$ CFI/ml. In some embodiments, the cell density in the suspension of pre-culture and polymeric substance solution is about $10^3$ to $10^4$ CFU/ml. In some embodiments, the cell density in the suspension of pre-culture and polymeric substance solution is about $10^4$ to $10^5$ CFU/ml. In some embodiments, the cell density in the suspension of pre-culture and polymeric substance solution is about $10^5$ to $10^6$ CFU/ml. In some embodiments, the cell density in the suspension of pre-culture and polymeric substance solution is about $10^6$ to $10^7$ CFU/ml. In some embodiments, the cell density in the suspension of pre-culture and polymeric substance solution is about $10^7$ to $10^8$ CFU/ml.

In particular, the pre-cultured microorganism is used without further purification. Specifically, for use in step a) the culture medium comprising the pre-cultured microorganism is diluted by suspending in a polymeric substance solution to a cell density of about $10^6$-$10^8$ CFU/ml.

A further embodiment of the invention relates to the method as described herein, wherein the biodegradable polymeric substance is selected from the group consisting of alginate, agarose, agar, gelatin, polyacrylamide, chitosan, and polyvinyl alcohol. In some embodiments, the polymeric substance is alginate. In some embodiments, the polymeric substance is sodium alginate.

A further embodiment of the invention relates to the method as described herein, wherein the polymeric substance solution is solidified by ionotropic gelation.

Specifically, the polymeric substance solution is gelled following addition of a multivalent ion solution.

In one embodiment of the invention, the multivalent ion solution is a $CaCl_2$ solution.

In one embodiment of the invention, the at least one microorganisms are bacterial and/or fungal cells.

In some embodiments, the at least one microorganisms are bacterial cells selected from the group consisting of *Azospirillum, Bacillus, Enterobacter, Stenotrophomonas, Rhizobium, Bradyrhizobium, Ensifer, Methylobacterium, Serratia, Lysobacter, Firmicutes, Azotobacter, Sphingomonas* and *Pseudomonas*, and the fungal cells are *Trichoderma* cells.

A further embodiment of the invention relates to the method as described herein, wherein at least two microorganisms of different origin are applied. Therefore, in one embodiment of the invention, bacterial cells from two, three, four, five, six, or more different species may be employed.

In an alternative embodiment of the invention, fungal cells from two, three, four, five, six, or more different species may be employed.

Alternatively, bacterial cells from one, two, three, four, five, six, or more different species may be employed together with fungal cells from one, two, three, four, five, six, or more different species. Thus, one, two, three, four, five, or more distinct individual organisms or distinct members of different genetic derivation or taxa are encapsulated in the polymeric particle.

A further embodiment of the invention relates to the method as described herein, wherein the encapsulated microorganisms are cultivated in in a fluidized-bed fermenter-like system. Specifically, the encapsulated microorganisms are in-bead cultivated until a cell density of about $10^9$ to $10^{12}$ CFU/g dry weight is reached.

According to a further embodiment of the invention the encapsulated microorganisms are in-bead cultivated until a cell density of about $10^{10}$, $10^{11}$ or $10^{12}$ CFU/g dry weight reached.

A further embodiment of the invention relates to the method as described herein, wherein the encapsulated microorganisms are cultivated at temperatures of 20° C.-30° C. for at least 24 to 72 hours. In some embodiments, the encapsulated microorganisms are cultivated at temperatures of 21-24° C. In some embodiments, the encapsulated microorganisms are cultivated for at least 36 hours. In some embodiments, the encapsulated microorganisms are cultivated for at least 48 hours. In some embodiments, the encapsulated microorganisms are cultivated for about 36 to 48 hours. In some embodiments, the encapsulated microorganisms are cultivated for about 48 to 72 hours.

In one embodiment of the invention, the in-bead cultivation is carried out with polymeric particles, wherein in said particles comprising microbial cells of one, two, three, four, five, six, or more distinct genetic origins have been encapsulated. The in-bead cultivation may be carried out with polymeric particles containing encapsulated microbial cells that share a common genetic derivation, e.g., one or more propagules of a single microbe, or polymeric particles which contain encapsulated microbial cells that have a divergent genetic derivation or taxonomic relationship. As a non-limiting example, a polymeric particle may contain one or more bacterial cell colonies having shared genetic derivation, a polymeric particle may contain one or more bacterial or fungal cell colonies having divergent genetic derivation (for example, one or more distinct species, genera, class, family, order or phylum).

A further embodiment of the invention relates to the method as described herein, wherein the encapsulated microorganisms in the polymeric particles possess a sessile lifestyle and establish dense multicellular aggregates due to the cultivation step. In particular, the microorganisms in the polymeric particles are embedded in a self-produced extracellular matrix.

The polymeric particles may be dried at ambient temperatures, preferably air dried. For example, the polymeric particles are dried in a static bed or drum dryer at a temperature of about 20 to 35° C., preferably at a temperature of about 25 to 30° C. The average drying time is of about 18 to 36 h, preferably of about 24 to 30 h. Thus, a further embodiment of the invention relates to the method as described herein, wherein the polymeric particles are dried, preferably air dried.

The dry polymeric particles have a moisture content of less than or equal to 15.0% by weight, based on the total weight of said polymeric particles. According to a further embodiment of the invention the dry polymeric particles have a moisture content of less than or equal to 20.0% by weight, or less than or equal to 10.0% by weight, based on the total weight of said polymeric particles.

The polymeric particles are advantageous for applications in the field of agriculture, food and/or feed industry, cosmetics industry and/or pharmaceutical industry.

A further embodiment of the invention relates to the use of the polymeric particles as described herein for targeted agricultural delivery, plant protection, growth promotion, and/or fertilization, biological remediation of soil and/or water, as food additives, feed additives, or for medical purposes.

In particular, the polymeric particles may be used in agricultural industry, e.g. for producing biological agents for plant health protection, plant growth promotion, biofertilization and a-biotic stress protection.

According to an aspect of some embodiments of the present invention there is provided a use of the polymeric particle as a medicament for treating a condition that is treatable by the encapsulated microbial cells.

BRIEF DESCRIPTION OF DRAWINGS

FIG. 12B Viability of a second *Pseudomonas* species ("strain B") after drying, after short term storage at 30° C., and after long term storage at 30° C. when formulated by the BFC technology using differing cultivation media (LB=Luria-Bertani broth, TSB=tryptic soy broth).

DESCRIPTION OF EMBODIMENTS

Figure 1A:
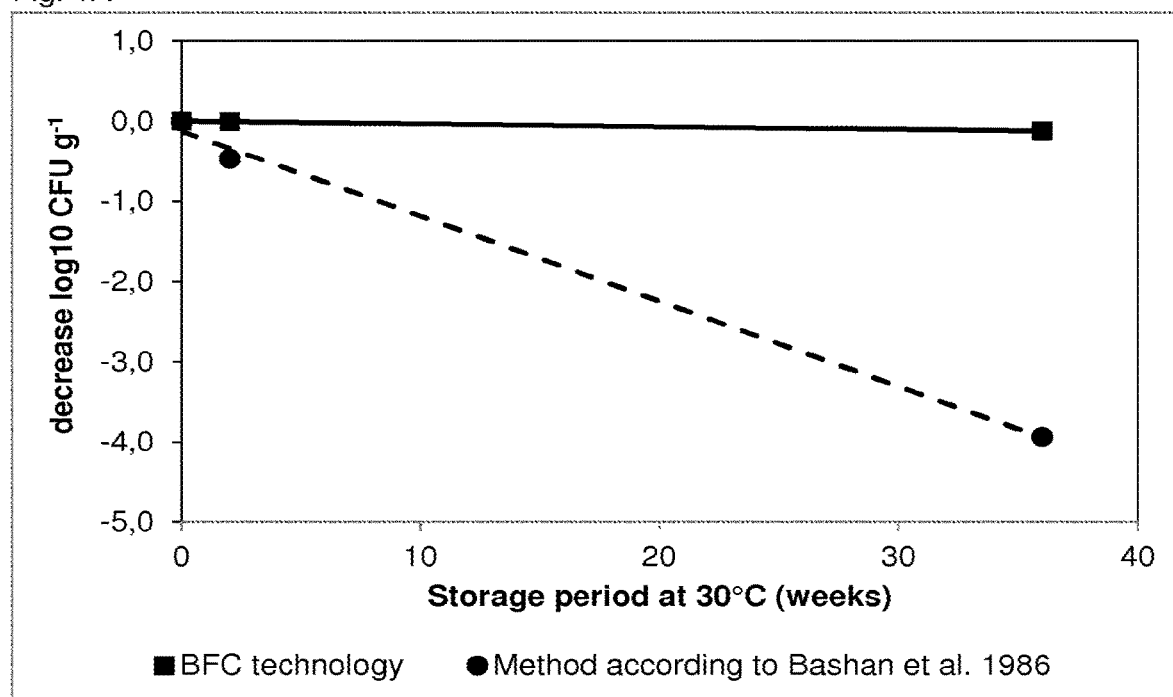
FIG. 1A: Viability of *Stenotrophomonas rhizophila* cells formulated by the encapsulation method according to Bashan et al 1986 (circle) and by the inventive bacterial fungal conservation (BFC) technology (square) at 30° C. over a period of 36 weeks.

The application of microorganisms for any purpose at commercial scale strongly depends on the reliability of the microbial preparation. Particularly, when microbial agents are intended to be applied as additive e.g. in coatings for seed treatment processes, the requirements for the formulation are high. Apart from the general desiccation stress in dry formulations, microorganisms are additionally exposed to physical, thermal as well as to detrimental chemicals, e.g., pesticidal agents. To circumvent said problems with the stability of microbial strains, mostly Gram-positive bacteria with spore-forming ability are currently used.

Conventionally, microbial agents are produced by cultivating microbial cells in liquid media to a certain cell number, harvesting, mixing with appropriate carriers and drying. The encapsulation of cells in biopolymers (e.g., sodium alginate) prior to drying is also commonly used (Bastian et al., 1986). To evoke longevity of the formulated microbes, several strain-specific protective compounds are applied. In case of multi-strain preparations, the single strains are usually cultivated individually before they are formulated together. Sensitive Gram-negative bacteria possess a great potential for biological plant protection. Despite much attention on the stabilization of microorganisms in formulations suitable for large scale applications, no appropriate solutions are available.

The invention discloses methods for formulation and fermentation to improve the viability of microbial cells during storage and application. In some embodiments, methods described herein comprise reducing pre-culture inoculation densities. In some embodiments, methods described herein comprise a step of in-bead cultivation of encapsulated microbial cells. Methods disclosed herein are suitable for all microorganisms including those for agricultural purposes, for food and feed purposes, as well as for medical purposes.

As used herein, the terms "microorganism" or "microbial" cover prokaryotic and eukaryotic, unicellular or multicellular organisms, and combinations thereof, which can be propagated and manipulated in a laboratory. In some embodiments, a microorganism includes, but is not limited to, eubacteria and archaea, protozoa, fungi and algae. In the present disclosure, the term microorganism typically denotes a live microorganism, e.g., capable of propagation, e.g., capable of having metabolic activity.

As used herein, the terms "bacteria" and "eubacteria" are used in reference to unicellular organisms, including recombinant organisms, lacking that lack a nucleus and other membrane bound organelles. Bacteria can function and reproduce as individual cells or multicellular aggregates.

As used herein "archaea" are single-cell organisms that lack nuclei and have archaeal membranes, specifically made of ether lipids.

As used herein, "fungi" is used in reference to eukaryotic organisms such as the molds and yeasts, including dimorphic fungi, fungi found in soil, recombinant fungi and any fungi capable of growing on plants.

As used herein, the term "strain" refers in general to a distinct genotype of organisms of the same species. More particularly, the term "strain" refers to members of a microbial species, wherein such members, i.e., strains, have different genotypes and/or phenotypes. Herein, the term "genotype" encompasses both the genomic and the recombinant DNA content of a microorganism and the microorganism's proteomic and/or metabolomic profile and post translational modifications thereof. Herein, the term "phenotype" refers to observable physical characteristics dependent upon the genetic constitution of a microorganism. As one skilled in the art would recognize, microbial strains are thus composed of individual microbial cells having a common genotype and/or phenotype. Further, individual microbial cells may have specific characteristics (e.g., a specific rep-PCR pattern) which may identify them as belonging to their particular strain. A microbial strain can comprise one or more isolates of a microorganism.

As used herein, the term "reference method" refers to an alternate method of microbial stabilization other than the inventive BFC technology described herein, e.g., an alternate method that does not include stabilizing microorganisms by shifting them into a dormancy-like state through targeted in-bead cultivation). A "reference composition" refers to a composition generated from an identical pre-culture material by application of a differing stabilization methodology. By way of a non-limiting example, stability of a microbial cells encapsulated in polymeric particles using a method of the present invention (e.g., stabilizing microorganisms by shifting them into a dormancy-like state through targeted in-bead cultivation) is compared to a reference composition wherein the reference composition was generated using a different method, such that differences in stability of the end-product microbial cells are attributable to differences in the method of production.

As used herein, the term "kingdom" refers to the general taxonomic category, e.g. fungi and bacteria.

As used herein, "CFU" refers to a colony forming unit.

As used herein, the term "inoculum" is intended to mean any form of microbial cells, or spores, which is capable of propagating in a culture medium.

Culture medium as used herein is defined as a mixture which supports the growth of microbial cells, such as disclosed microorganism, said mixture may contain for example ingredients such as peptone, soy peptone, molasses, potato starch, yeast extract powder, glucose, mannitol, skim milk or combinations thereof. Culture medium can be solid culture medium or liquid medium.

According to the invention there are provided microorganisms, such as for example, but not limited to, biotechnologically, agriculturally or medically useful microorganisms, microorganisms useful for food and teed purposes, which are encapsulated in biodegradable polymers.

Microorganisms of the invention can either be of natural origin or produced by recombinant methods.

As used herein, the term "biodegradable polymer" refers to polymer-based matrices that show at least some biodegradability. Non-limiting examples of suitable biodegradable polymers include collagen, gelatin, alginate, polycaprolactone, and poly lactic-co-glycolic acid (PLGA).

In some embodiments, the biodegradable polymer may be an unsaturated biodegradable polymer (i.e. a biodegradable polymer containing at least one unsaturated carbon-carbon bond, such as a double or a triple bond). Such unsaturated polymers may be cross-linkable in situ. Non-limiting examples of unsaturated biodegradable polymers include poly-propylene fumarate (PPF), poly(ζ-caprolactone-fumarate), and mixtures and co-polymers thereof.

In various embodiments, the polymer particles of the present invention may be hydrogel particles (e.g., alginates, fibrins, and gelatins), natural or synthetic biodegradable particles (e.g., particles derived from or coated with poly lactic-co-glycolic acid (PLGA)), biodegradable porous particles (e.g., silicon porous particles), and biocompatible vesicles (e.g., liposomes and/or micelles).

Particularly suitable biodegradable polymers for agriculturally suitable microorganisms are, amongst others, agarose, alginates, agar, gelatin, polyacrylamide, kappa-carrageenan, furcellaran, 2-methyl-5-vinyl-pyridine-methylacrylate, ethyl succinylated cellulose, chitosan, polyvinyl alcohol, polygammaglutamic acid, ethyl cellulose and other biodegradable polymers known to one of skill in the art.

Alginate is a naturally occurring anionic polymer typically obtained from brown seaweed. Due to its biocompatibility, low toxicity, relatively low cost, and mild gelation by addition of divalent cations such as $Ca^{2+}$ it has been extensively used for many biomedical applications. Commercially available alginate is typically extracted from brown algae (Phaeophyceae). Alginate with more defined chemical structures and physical properties can be obtained from seaweed-derived alginate. Bacterial alginate can be produced from *Azotobacter* and *Pseudomonas*.

Alginate is a mix-polysaccharide composed of D-mannuronic acid (M) L-guluronic acid (G). The main alginate series include sodium alginate, potassium alginate, calcium alginate, ammonium alginate etc. In some embodiments sodium alginate is used.

For medical purposes, the biodegradable polymer is selected from materials which are considered safe to the human body and degraded in the body for a certain period of time. Examples of biodegradable polymers considered safe include albumin, collagen, gelatin, fibrinogen, casein, fibrin, hemoglobin, transferrin, chitin, chitosan, hyaluronic acid, heparin, chondroitin, keratin sulfate, alginate, starch, dextrin, dextran, polylactic acid, polyglycolic acid, lactic acid-glycolic acid copolymer, polyhydroxybutyric acid, polycaprolactone, polyanhydride and polyalkylcyanoacrylate.

Individual polymeric particles may be produced when specified hydrogel polymers are complexed in solutions of biologically active substrates. An alginate solution, for example, will form a gel when a complexing agent is added. Calcium chloride ($CaCl_2$) is generally used; however, lanthanum chloride, ferric chloride, cobaltous chloride and calcium hydroxide are also acceptable.

In order to obtain alginate beads which include microbial cells, the microbial cells are dispersed in a sodium alginate solution. The obtained solution is dropped into a crosslinking solution containing divalent cations, e.g. $Ca^{2+}$. Solidification of the droplets starts immediately on the droplet surface by ionotropic gelation. $Ca^{2+}$ reacts with the negatively charged polymer chains to form a three-dimensional rigid structure.

In one embodiment of the invention, the microbial cells are individually pre-cultured according to conventional methods up to a cell density of about $10^9$ to $10^{10}$ CFU/ml.

The individual pre-cultures are suspended in a biodegradable polymer solution up to a cell density of about $10^6$ to $10^8$ CFU/ml. Thus, in one embodiment two pre-cultures of microorganism of different origin are suspended in the biodegradable polymer solution, e.g., in an alginate solution. In some embodiments, 3, 4, 5, 6, or more microorganism of different origin are suspended in an alginate solution. Optionally, the polymer solution contains additionally carriers and/or additives.

If 2 microorganisms of different origin are provided, they may be present in a ratio of 1:5 to 5:1, or 1:2 to 2:1, or 1:1. If 3 microorganisms of different origin are provided, they may be present in a ratio of 1:1:5 to 5:5:1, or 1:2:2 to 2:1:1, or 1:1:1, etc.

Various additives such as adherents, dispersants, surfactants, and nutrient and buffer ingredients, can also be included. Trace nutrients such as salts of iron, manganese, boron, copper, cobalt, molybdenum, or zinc may be added. Other conventional additives including, but not limited to, coating agents, wetting agents, buffering agents, and polysaccharides may be added. At least one agriculturally acceptable carrier can be added to the formulation such as water, solids or dry powders. The dry powders can be derived from a variety of materials such as calcium carbonate, gypsum, fluency agent, vermiculite, talc, clay, humus, activated charcoal, and various phosphorous compounds. These additives are generally added to the suspension in an amount of 0.001% to 10% of the polymeric substance solution.

Suitable carriers include, but are not limited to mineral earths such as silica, silica gels, silicates, talc, kaolin, attaclay, limestone, chalk, loess, clay, dolomite, diatomaceous earth, calcium sulfate, magnesium sulfate, magnesium oxide, ground synthetic materials, fertilizers such as ammonium sulfate, ammonium phosphate, ammonium nitrate, thiourea and urea, products of vegetable origin such as cereal meals, tree bark meal, wood meal and nutshell meal, cellulose powders, attapulgites, montmorillonites, mica, vermiculites, synthetic silica and synthetic calcium silicates, or compositions of these.

Bead formation is performed for example by dropping the suspension, which comprises the pre-cultured microbial cells and a polymeric substance, into a multivalent ion solution bath using a vibrating nozzle. In some embodiments, the nozzle diameter may be in the range of about 1 µm to 500 µm. In some embodiments the nozzle diameter is within the range of 70 to 100 µm. In some embodiments the nozzle diameter is about 75 µm. In some embodiments the nozzle diameter is about 100 µm. In some embodiments the nozzle diameter is about 200 µm and the obtained wet beads have an average diameter of about 100 to 500 µm.

Bead diameters of less than 500 µm and preferably less than 100 µm may be advantageous because they allow optimal growth of bacteria across the entire bead and, thus, use full capacity of bead volume to achieve a maximum of bacterial load. A prerequisite for uniform growth is uniform allocation of nutrients and oxygen. The polymer matrix acts as a diffusion barrier limiting the transfer of compounds within the beads. It can be assumed that the concentration of nutrients and oxygen in particular, decreases from the outer layer to the bead core. The larger the diameter of the beads the lower the concentration of growth compounds in the inner parts, e.g., in the core of the beads. Insufficient availability of nutrients would impair bacterial growth and cause barren zones. In consequence, the larger the diameter of the beads the lower the volumes in which bacteria are able to multiply in relation to the total volume of the bead. The achievable cell number per gram polymeric particles is lower in beads with an average diameter greater than 500 µm, compared to beads with an average diameter less than 500 µm.

After a washing step, the obtained beads are transferred to a system for cultivation of the encapsulated microorganisms. The incubation time is of about 12 to 120 hours, preferably of about 48 hours. Suitable systems for in-bead cultivation of encapsulated microorganisms are, for example: fluidized bed reactors. Due to process-specific cultivation, the encapsulated microorganisms' stability is enhanced via stress adaptation. The growth rates and maximal cell counts resemble those from non-encapsulated cultures but can be slightly higher. Additionally, microbial cells that are allowed to multiply in a solid matrix format may induce biofilm-like substances and demonstrate improved shelf-life of the particle as described herein.

Batch fermentation processes represent closed systems, in which bacterial cultures pass through different growth phases. In the moment, the conditions become unfavorable e.g., nutrients are exhausted and waste products are enriched, bacteria populations enter the stationary phase characterized by stable cell numbers over a certain period of time. Such conditions induce a general stress-response in bacterial cells and an adaptation of their metabolic activity in preparation of a starvation period. Stress-mediated response involves changes in cell membrane structure, formation of biofilms and synthesis of compounds protecting essential molecules such as proteins and DNA. Stress-adapted cells possess a higher tolerance towards adverse conditions and a higher survivability.

Thus, the duration of the cultivation process of bacteria within the beads is not determined by the end of the multiplication (begin of stationary phase) with the aim to obtain the maximum of cell numbers. As described herein, the inventors made the novel and unexpected discovery that by prolonging in-bead cultivation the stationary phase is subsequently maintained enabling bacteria to activate mechanisms and to adapt to stress conditions, and to exhibit the so-called stationary phase phenotype.

The time a culture needs to accomplish stress-adaptation and the underlying mechanisms are strain-specific, they have to be adapted to the respective microbial strains. For the majority of microorganisms a time period between 48 and 72 hours is sufficient for in-bead cultivation.

A biofilm is a well-organized community of microorganisms that adheres to surfaces and is embedded in a matrix of extracellular polymeric substances (EPSs). EPSs are a complex mixture of high-molecular-mass polymers (>10,000 Da) generated by the bacterial cells, cell lysis and hydrolysis products, and organic matter adsorbed from the substrate. EPSs are involved in the establishment of stable arrangements of microorganisms in biofilms. Biofilm formation is one of the mechanisms bacteria use to survive in adverse environments. Bacteria living in a biofilm usually have significantly different properties from free-floating (planktonic) bacteria of the same species, as the dense and protected environment within the biofilm allows them to cooperate and interact in various ways. One benefit of this environment is increased resistance to detergents and antibiotics, as the dense extracellular matrix and the outer layer of cells protect the interior of the community.

Figure 5:
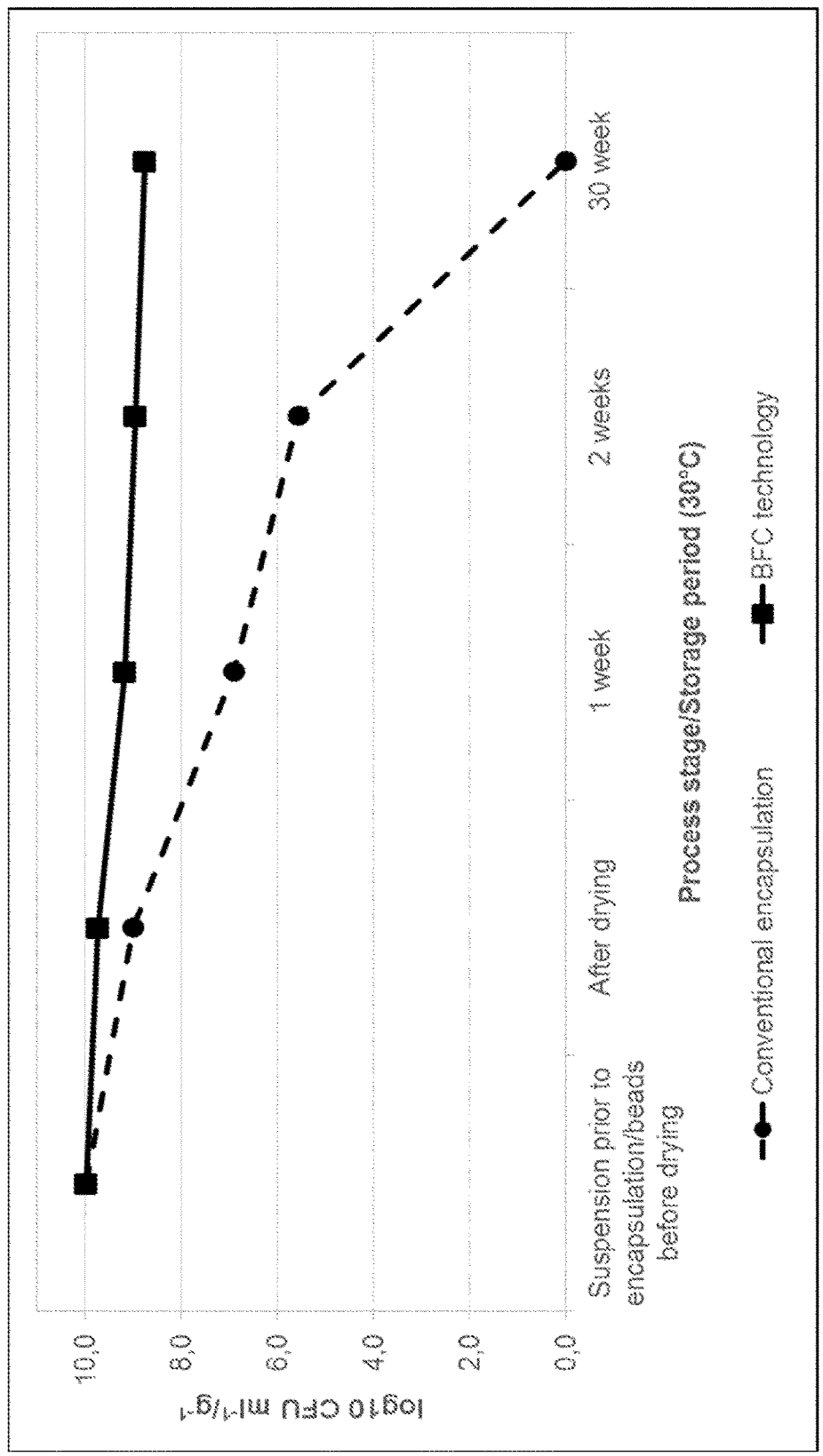
FIG. 5 Viability of *Rhizobium fredii* DSM 5851 cells formulated by encapsulation of planktonically grown cells ("conventional encapsulation") (circle) and by the inventive BFC technology (square) at 30° C. over a period of 30 weeks. For each encapsulation methodology the beads had a diameter of approximately 200 μm after drying, and between 480-600 μm when wet (prior to drying).
Figure 6:
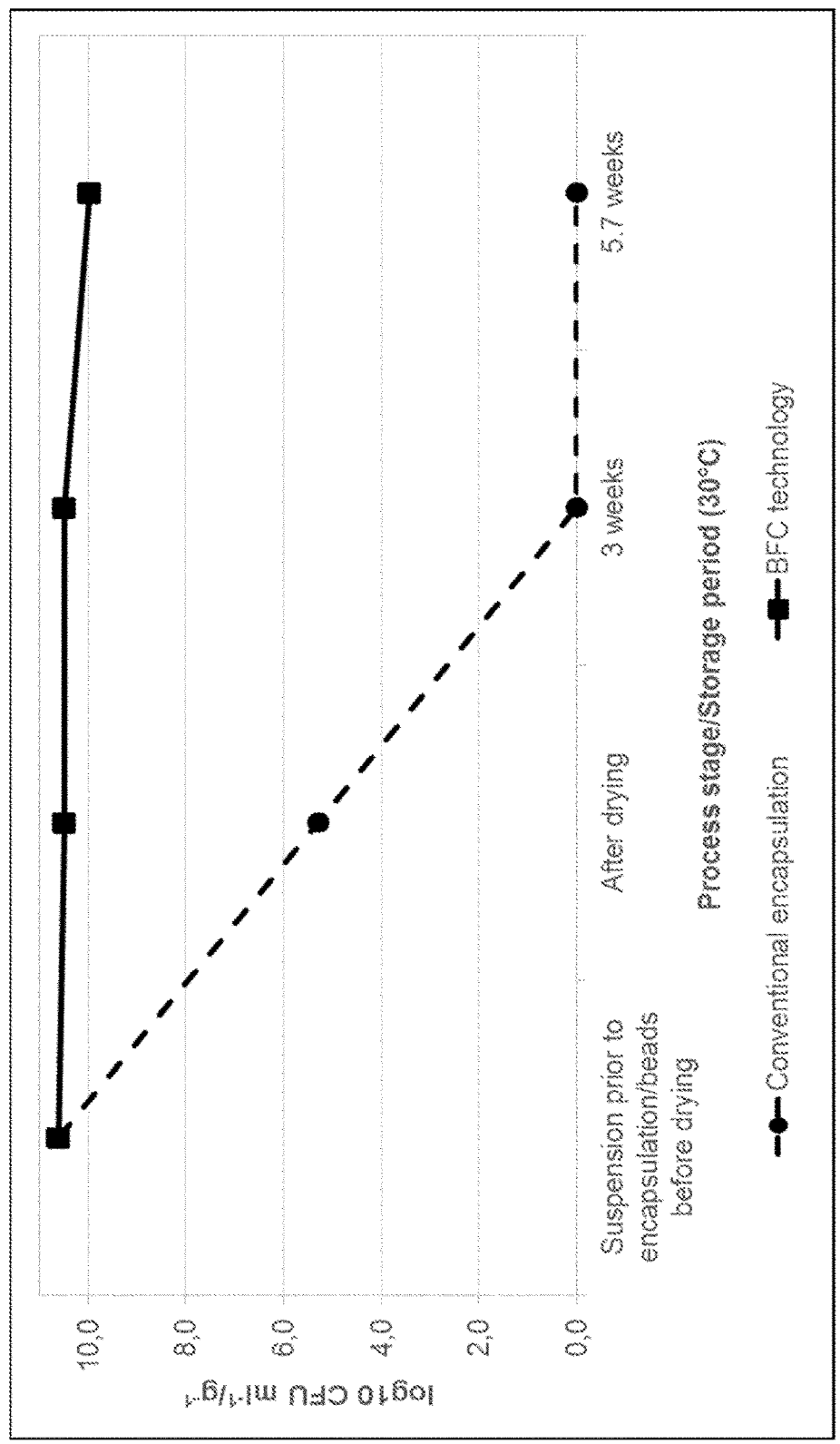
FIG. 6 Viability of *Enterobacter cowanii* cells formulated by encapsulation of planktonically grown cells ("conventional encapsulation") (circle) and by the inventive BFC technology at 30° C. over a period of 40 days. For each encapsulation methodology the beads had a diameter of approximately 200 μm after drying, and between 480-600 μm when wet (prior to drying).
Figure 7:
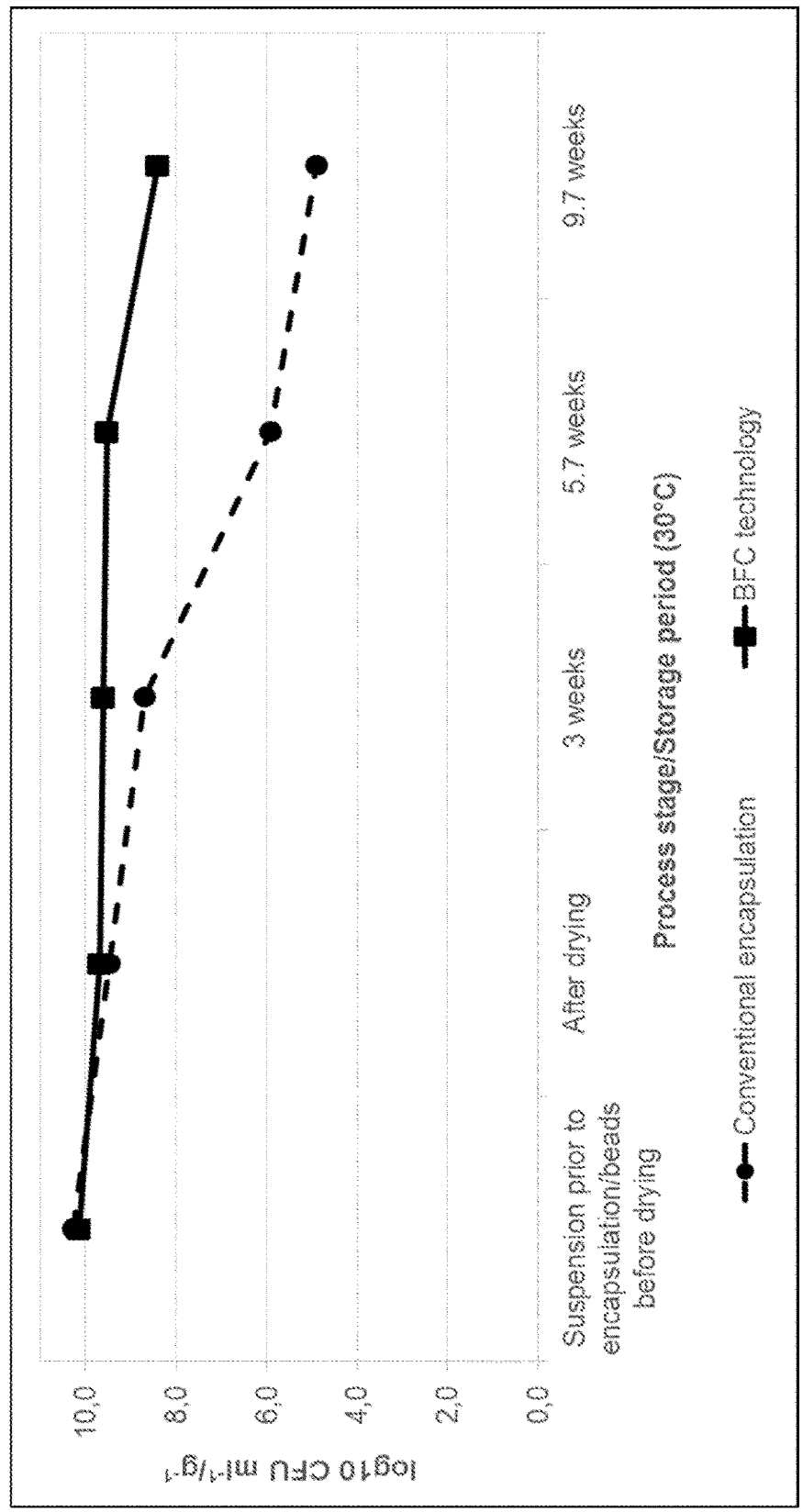
FIG. 7 Viability of *Sphingomonas sanguinis* cells formulated by encapsulation of planktonically grown cells ("conventional encapsulation") (circle) and by the inventive BFC technology at 30° C. over a period of 68 days. For each encapsulation methodology the beads had a diameter of approximately 200 μm after drying, and between 480-600 μm when wet (prior to drying).
Figure 8A:
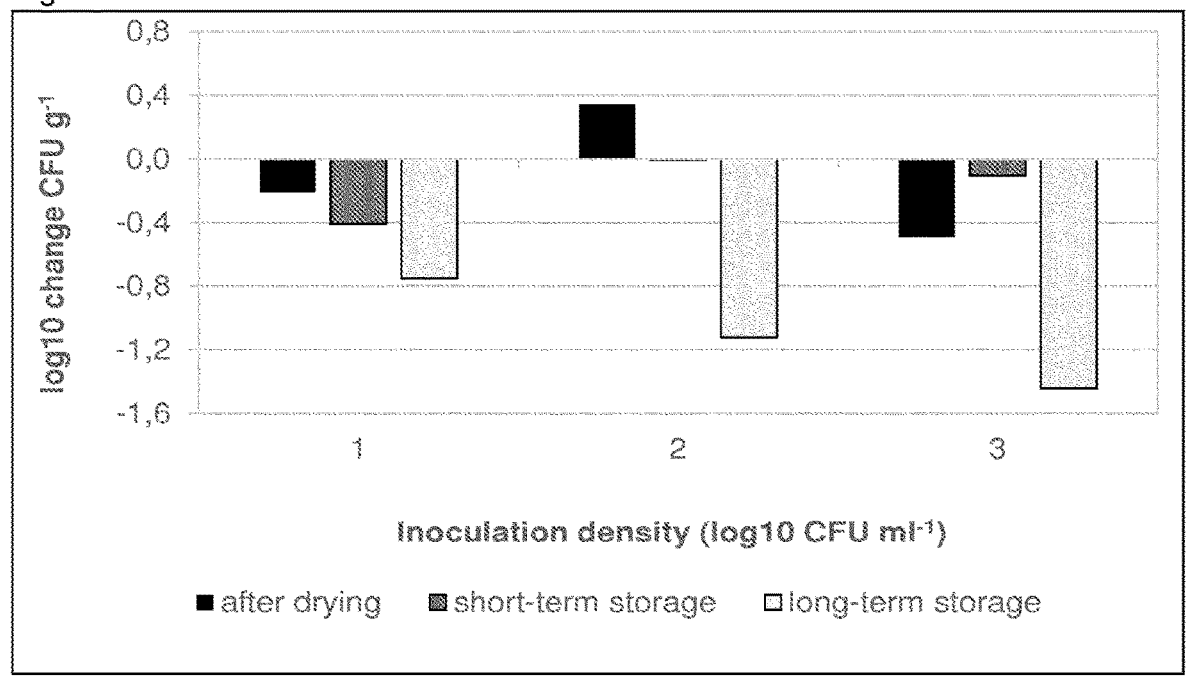
FIG. 8A Viability of a first *Pseudomonas* species ("strain A") when formulated by the BFC, technology using differing pre-culture inoculation densities ($10^5$ CFU/mL, $10^6$ CFU/mL, $10^7$ CFU/mL) after drying, after short term storage at 30° C., and after long term storage at 30° C.
Figure 8B:
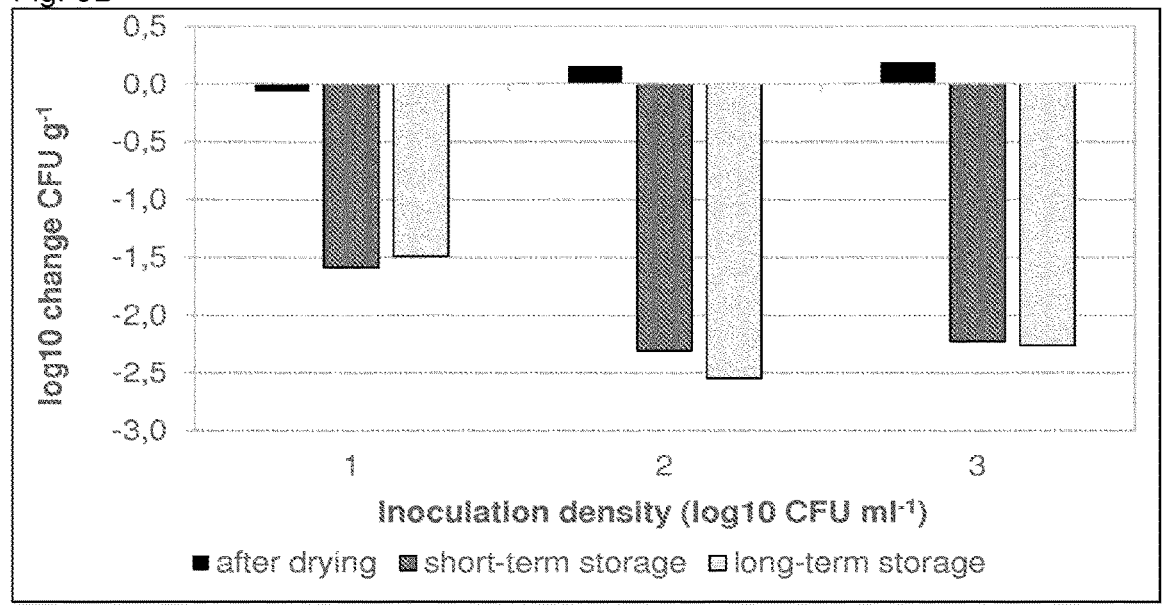
FIG. 8B Viability of a second *Pseudomonas* species ("strain B") when formulated by the BFC technology using differing pre-culture inoculation densities ($10^5$ CFU/mL, $10^6$ CFU/mL, $10^7$ CFU/mL) after drying, after short term storage at 30° C., and after long term storage at 30° C.
Figure 9:
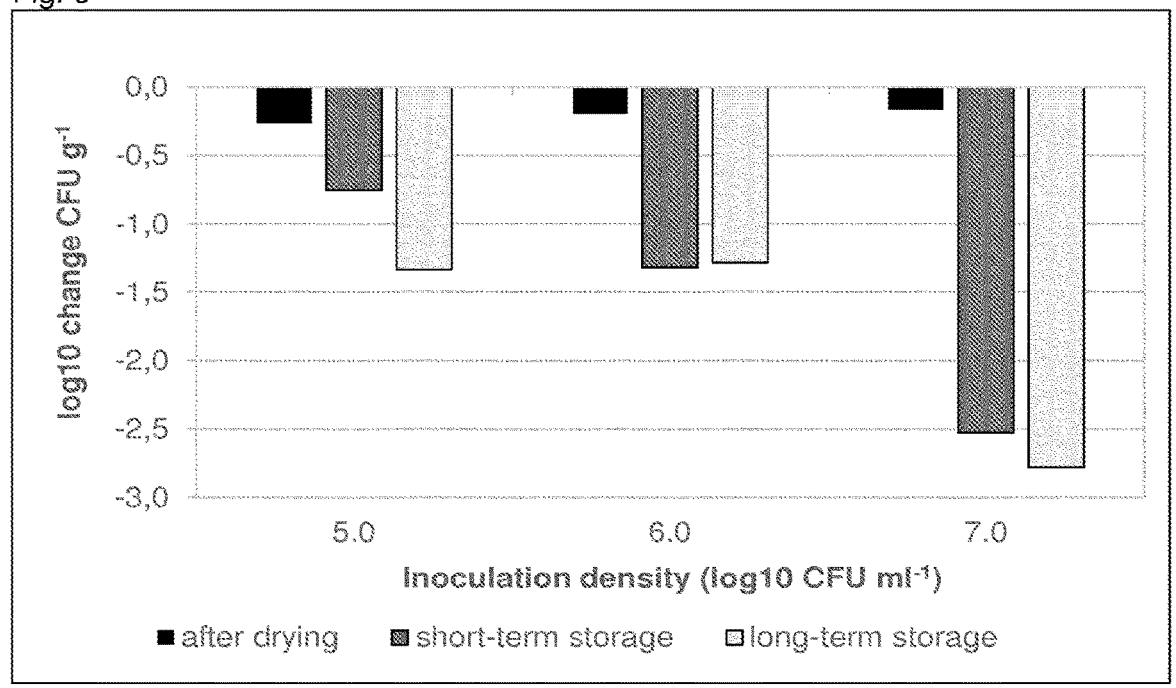
FIG. 9 Viability of a *Serratia* species when formulated by the BFC technology using differing pre-culture inoculation densities ($10^5$ CFU/mL, $10^6$ CFL/mL, $10^7$ CFU/mL) after drying, after short term storage at 30° C., and after long term storage at 30° C.
Figure 10:
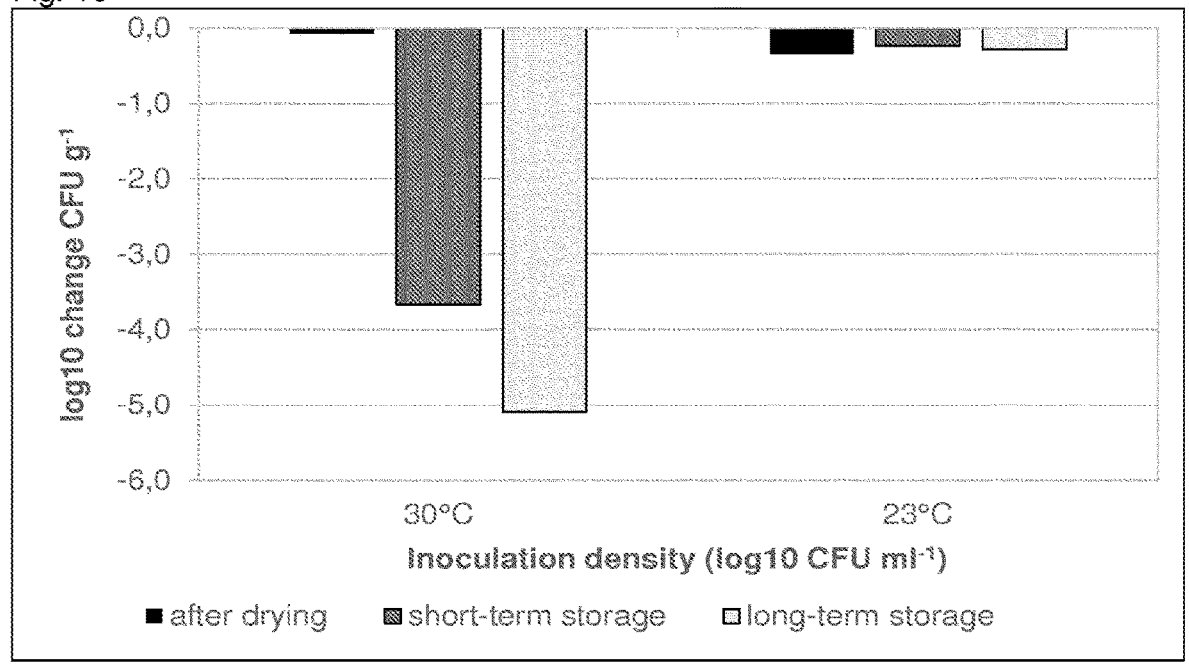
FIG. 10 Viability of *Stenotrophomonas rhizophila* SPA-P69 after drying, after short term storage at 30° C., and after long term storage at 30° C. when formulated by the BFC technology using differing cultivation temperatures (30° C. and 23° C.).
Figure 11:
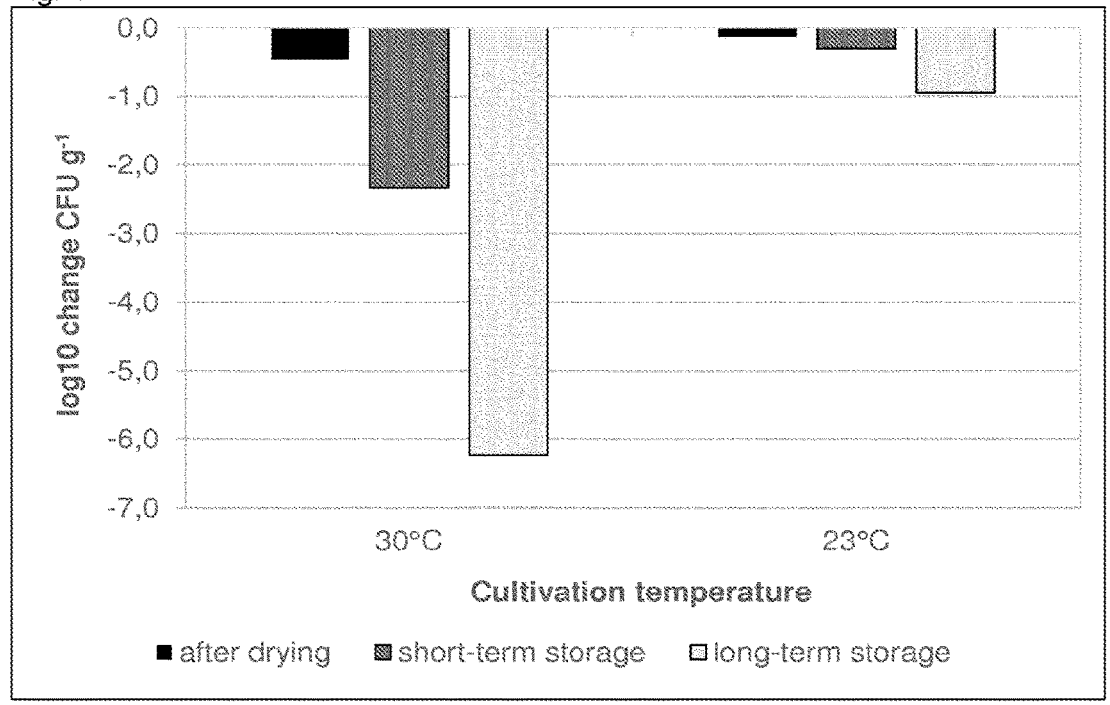
FIG. 11 Viability of *Rhizobium fredii* DSU 5851 after drying, after short term storage at 30° C., and after long term storage at 30° C. when formulated by the BFC technology using differing cultivation temperatures (30° C. and 23° C.).
Figure 12A:
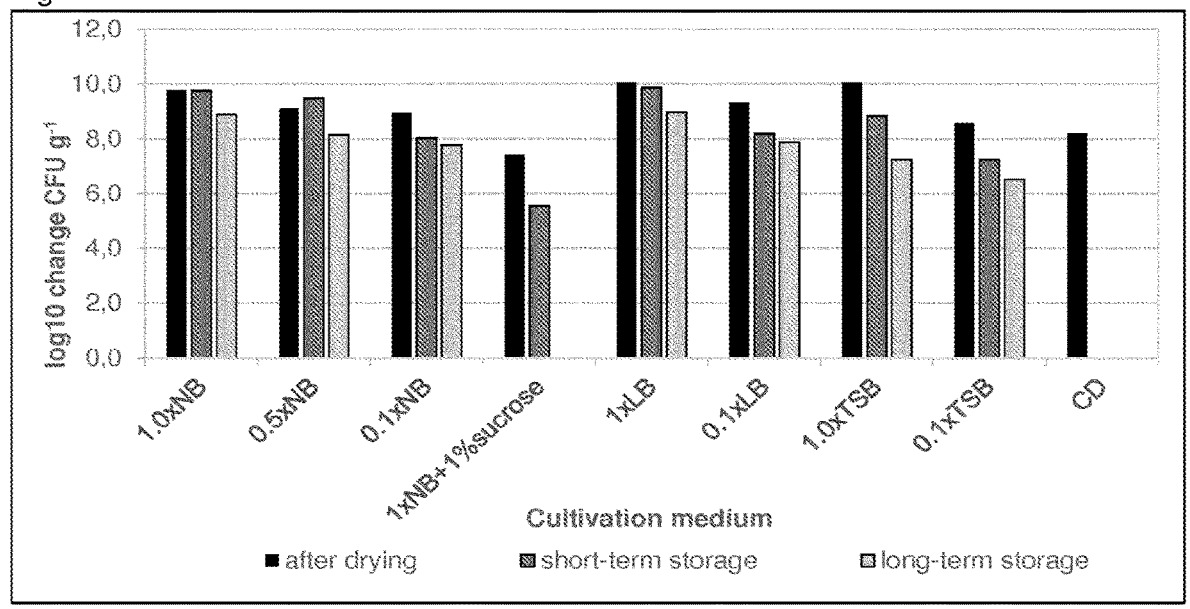
FIG. 12A Viability of a first *Pseudomonas* species ("strain A") after drying, after short term storage at 30° C., and after long term storage at 30° C. when formulated by the BFC technology using differing cultivation media (LB=Luria-Bertani broth, TSB=tryptic soy broth, CD=Czapek dox broth).
Figure 13:
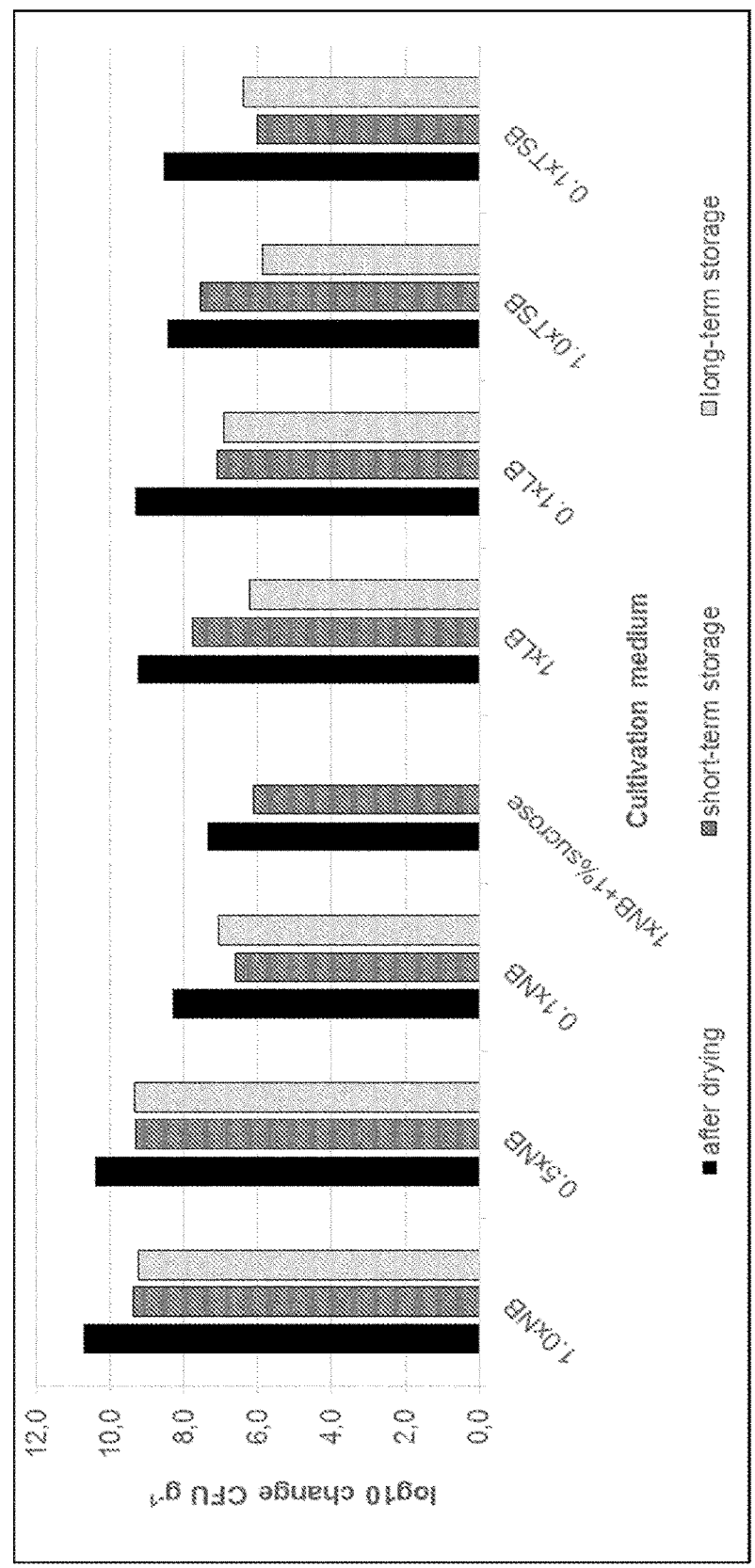
FIG. 13 Viability of a *Serratia* species after drying, after short term storage at 30° C., and after long term storage at 30° C. when formulated by the BFC technology using differing cultivation media (LB=Luria-Bertani broth, TSB=tryptic soy broth).

Bashan (1986) discloses the immobilization and multiplication of *Azospirillum brasilence* Cd in alginate heads. In Bashan (1986), *A. brasilence* was pre-cultured in nutrient broth to a final concentration of $10^9$ CFU/ml, then encapsulated in alginate beads. The beads were washed and incubated for 24 to 48 h in fresh nutrient broth medium to allow multiplication inside the beads. The beads were either kept in hermetically sealed flasks or were lyophilized and were stable for about 12 weeks (Bashan (1986), page 1095, FIG. 5B). However, if the particles were air dried, only a very small number of bacteria survive (Bashan (1986), page 1095, FIG. 5A).

In contrast, the beads obtained according to the present invention exhibit significant post-drying stability and may be dried at ambient temperatures and still are stable for at least 35 weeks at 30° C. as shown in FIG. 1A. For example, the beads are dried at 20 to 35° C. in a static bed or drum dryer, or at 25 to 30° C. The appropriate drying time is of about 15 to 48 h, or 22 to 36 h, or 24 to 30 h.

In contrast to Bashan (1986), the polymeric particles according to the invention can be stored at room temperature for several weeks without substantially reducing the number of viable microorganism cells.

A further embodiment of the invention relates to the polymeric particles comprising at least one microorganism, wherein at least 70% of the microbial cells in the beads are viable upon storage of at least 35 weeks at 30° C. In some embodiments at least 75%, 80%, 85%, 90%, or 95% of the microbial cells in the beads are viable upon storage of at least 35 weeks. In some embodiments at least 75%, 80%, 85%, 90%, or 95% of the microbial cells in the beads are viable upon storage of at least 35, 40, 45, 50 or 52 weeks at 30° C.

A further embodiment of the invention relates to the polymeric particles comprising at least two microorganisms of different origin, wherein at least 70% of the microbial cells in the beads are viable upon storage of at least 35 weeks at 30° C. In some embodiments at least 75%, 80%, 85%, 90%, or 95% of the microbial cells in the beads are viable upon storage of at least 35 weeks at 30° C. In some embodiments at least 75%, 80%, 85%, 90%, or 95% of the microbial cells in the beads are viable upon storage of at least 35, 40, 45, 50 or 52 weeks at 30° C.

in various embodiments the bacteria or fungi are agriculturally and/or horticulturally useful, for example, the bacteria are pesticidal and/or insecticidal, and/or supports plant growth and/or development, or any combination thereof.

In various embodiments the one or more bacteria may comprise *Serratia* (for example, *Serratia entomophilia* or *Serratia proteomaculans*), *Xanthamanas*, *Pseudomonas*, *Rhizobium*, *Bifidobacterium*, *Lactobacillus*, *Streptococcus* (*Enterococcus*), *Yersinia* (for example, *Yersinia entomophaga*), *Pseudomonas*, *Bacillus*, *Pasteuria*, *Azobacter*, *Enterobacter*, *Azospirillum*, *Cyanobacteria*, *Paecilomyces*, *Streptomycetes*, *Chromobacterium*, *Rhanella*, *Burkholderia*, *Paenibacillus*, *Collimonas*, *Sinorhizobium*, *Pantoea*, *Erwinia*, *Pediococus*, *Leuconostoc*, *Aeromonas*, *Neptunomonas*, *Klebsiella*, *Ponchonia*, *Brevibacillus*, *Acinetobacter*, *Paraburkholderia*, *Herbaspirillum*, *Bradyrhizobium*, *Methylobacterium*, *Ensifer*, *Sphingomonas*, *Azobacter*, *Lysobacter*, *Stenotrophamonas*, or any combination of two or more thereof.

In various embodiments the one or more fungi may comprise *Beauveria*, *Penicillium*, *Metarhizium*, *Trichoderma*, *Gliocladium*, *Coniothyrium*, *Paecilomyces*, *Verticillum*, *Sclerotinia*, and mycorrhizae or any combination of two or more thereof.

Bacterial and fungal microorganism suitable for use in the present invention preferably are selected from one or more genera of *Azotobacter*, *Bacillus*, *Stenotrophomonas*, *Serratia* and *Pseudomonas*, in addition to specific bacteria and fungi such as *Pseudomonas fluorescens*, *Azotobacter*, *Bacillus polymyxa*, *Stenotrophomonas rhizophila*, *Serratia plym-*

*uthica, Trichoderma herzianum, Trichoderma viride* respectively, or any combination thereof.

Figure 1B:
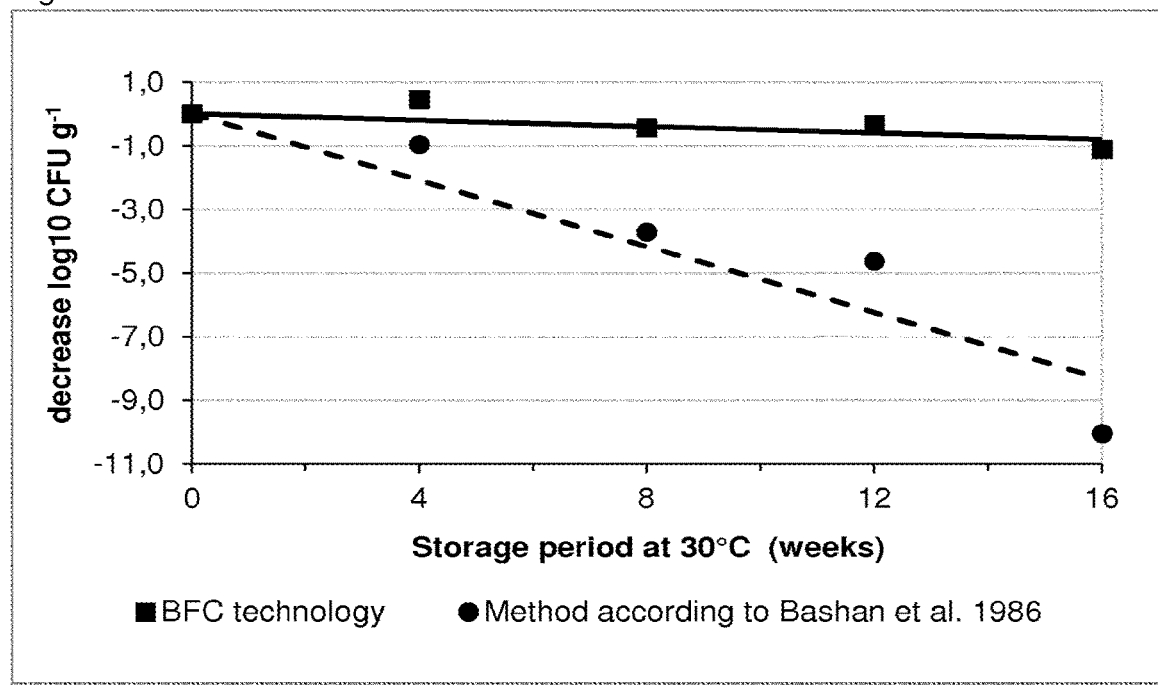
FIG. 1B: Viability of *Methylobacterium extorquens* Rah1 cells (Flavor enhancing bacterium for strawberry) formulated by the encapsulation method according to Bashan et al 1986 (circle) and by the inventive bacterial fungal conservation (BFC) technology (square); Storage conditions: 16 weeks at 30° C.
Figure 1C:
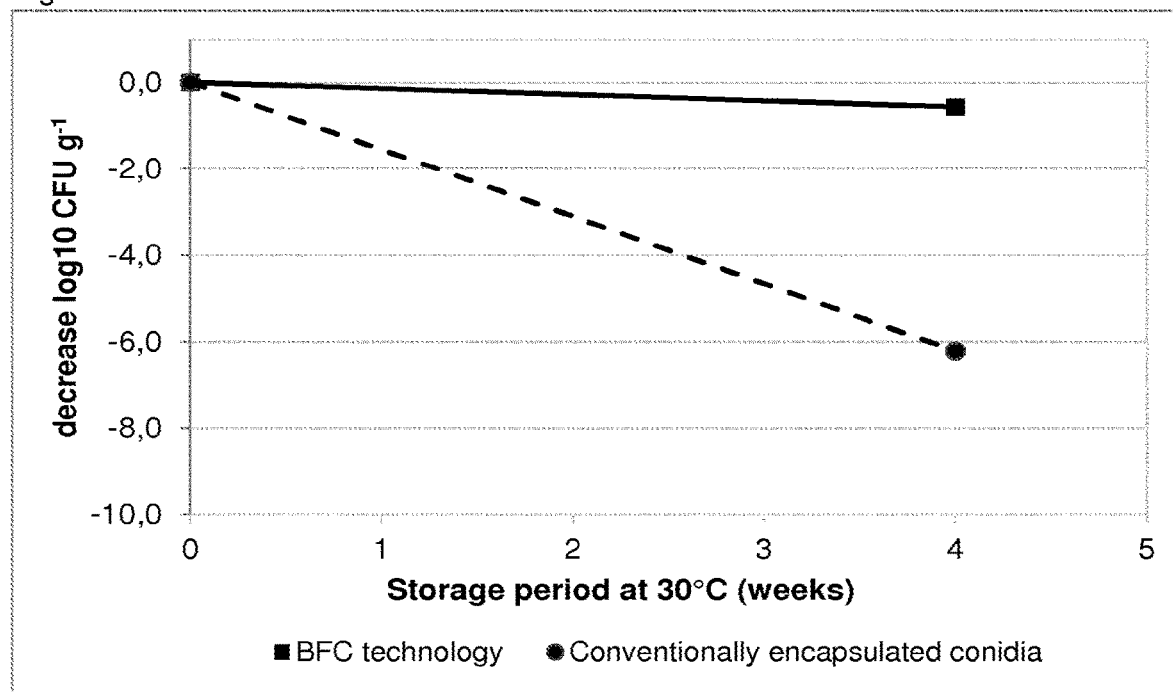
FIG. 1C: Viability of *Trichoderma* sp. (plant-growth promoting fungus) of conventionally encapsulated conidia (circle) and by the inventive bacterial fungal conservation (BFC) technology (square); Storage conditions: 4 weeks at 30° C.
Figure 2:
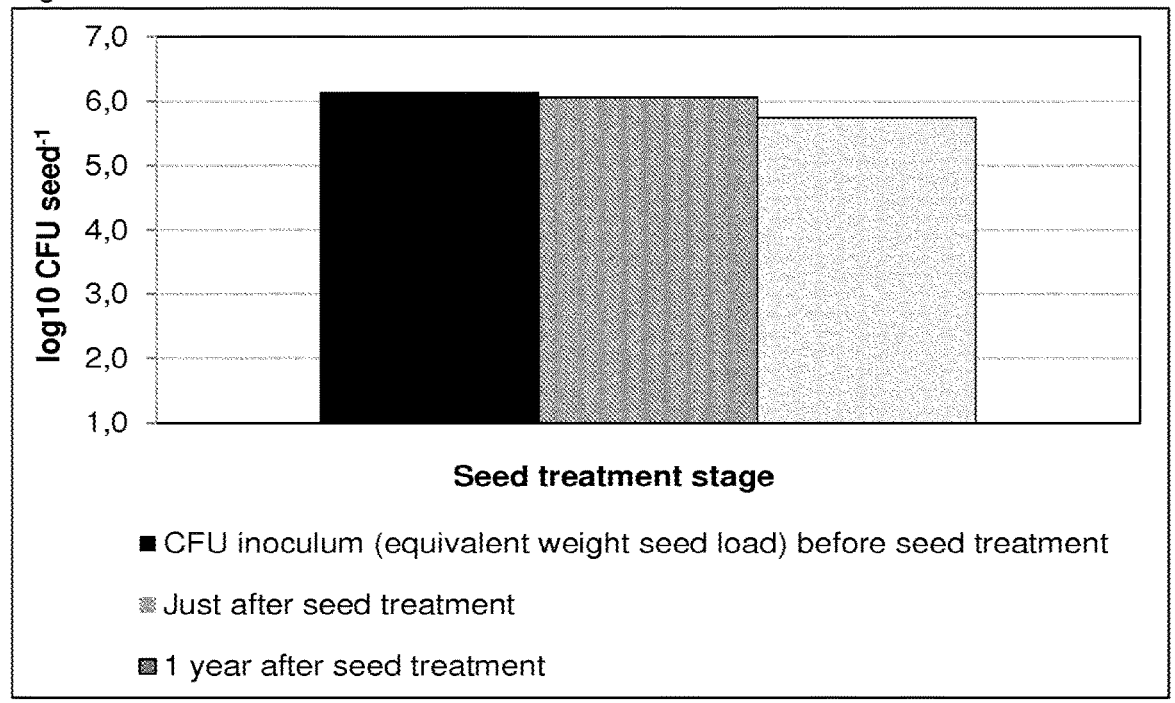
FIG. 2: Development of the viable cell counts over different stages of the product history starting from the dried product to one year after seed treatment. The cell numbers are specified as CFU per seed.
Figure 3:
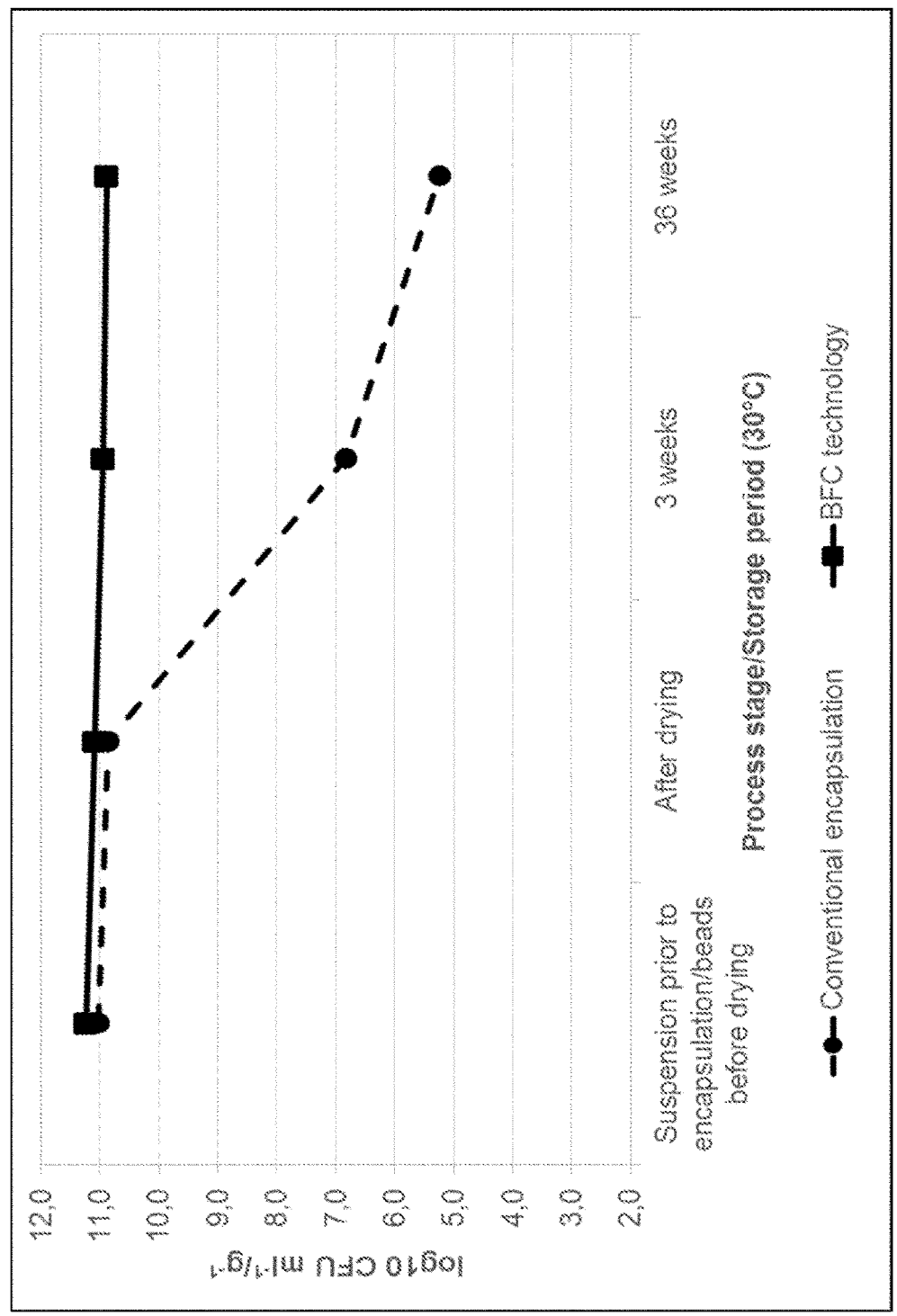
FIG. 3: Viability of *Stenotrophomonas rhizophila* cells formulated by encapsulation of planktonically grown cells ("conventional encapsulation") (circle) and by the inventive BFC technology (square) at 30° C. over a period of 36 weeks. For each encapsulation methodology the beads had a diameter of approximately 200 μm after drying, and between 480-600 μm when wet (prior to drying).
Figure 4:
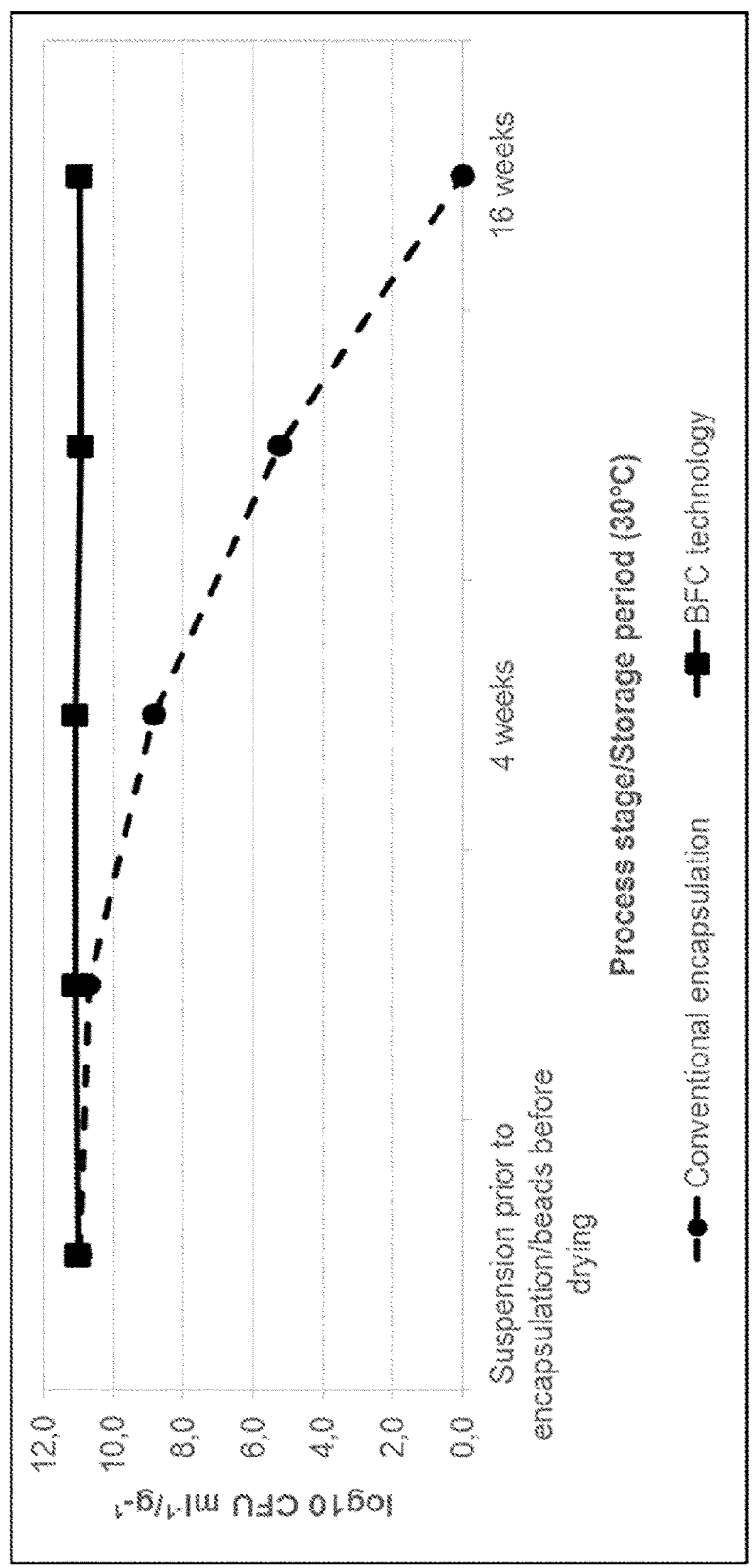
FIG. 4: Viability of *Methylobacterium extorquens* Rab1 cells formulated by encapsulation of planktonically grown cells ("conventional encapsulation") (circle) and by the inventive BFC technology (square) at 30° C. over a period of 16 weeks. For each encapsulation methodology the beads had a diameter of approximately 200 μm after drying, and between 480-600 μm when wet (prior to drying).

Using the present formulation method, the viability of microbial cells during storage and field application is improved compared to conventional method (see FIGS. 1A and 1B). The method is particularly suitable for sensitive microorganisms, such as Gram-negative bacteria but also fungi. Microbial cells formulated by that methods show survival rates during storage and when applied to seeds superior to other known methods. Moreover, due the compatibility with a broad range of strains the method allows a simultaneous formulation and cultivation of more than one microbial strain in a single preparation. Thus, the costs for the production of multi-strain preparation is reduced compared to individual cultivation approach.

EXAMPLES

The Examples which follow are set forth to aid in the understanding of the invention but are not intended to, and should not be construed to limit the scope of the invention in any way. The Examples do not include detailed descriptions of conventional methods, e.g., cultivation of microorganisms. Such methods are well known to those of ordinary skill in the art.

Example 1

Shelf-Life of Microorganisms Formulated by Bacterial and Fungal Conservation (BFC) Technology Results from strains with strain-specifically optimized fermentation and formulation parameter.

The potential of the stabilization formulation technology is exemplary demonstrated for selected plant-beneficial strains. The viability of microbial cells (CFU/g) produced by the invented technology was compared to conventionally encapsulated cells according to Bashan et al. (1986). Depending on the initial objective of a study, preparations were stored for different periods of time at 30° C..

Microbial cells propagated and formulated by the methods described herein show survival rates during storage and when applied e.g. to seeds superior to other known methods. Moreover, the methods described herein allow a simultaneous cultivation of more than one microbial strain in a single device. The invention involves two main concepts: i) a combined formulation and fermentation approach that enhances shelf-life stability and elevates the tolerance of formulated microbial cells towards desiccation and adverse effects during storage and application and ii) a method to cost-effectively cultivate more than one microbial strains in a single device. In a first step, individual pre-cultures from bacteria or fungi are obtained and suspended with a polymer solution that may contain additional carriers and additives. In some embodiments, the polymer solution is a 1.5-5% solution. In some embodiments, the polymer solution is an alginate solution. In some embodiments, the alginate solution is sodium alginate. In some embodiments, the sodium alginate solution is a 1.5-5.0% solution. Depending on the strain(s) to be inoculated the cell density is adjusted to $10^0$ to $10^8$ CFU/ml. In some embodiments, inoculation cell density is adjusted to about $10^4$ to $10^8$ CFU/ml. In some embodiments, inoculation cell density is adjusted to about $10^3$ to $10^7$ CFU/ml. In some embodiments, inoculation cell density is adjusted to about $10^2$ to $10^6$ CFU/ml. In some embodiments, inoculation cell density is adjusted to about $10^1$ to $10^5$ CFU/ml. In some embodiments, inoculation cell density is adjusted to about $10^0$ to $10^4$ CFU/ml. In some embodiments, inoculation cell density is adjusted to about $10^5$ to $10^8$ CFU/ml. In some embodiments, inoculation cell density is adjusted to about $10^4$ to $10^7$ CFU/ml. In some embodiments, inoculation cell density is adjusted to about $10^3$ to $10^6$ CFU/ml. In some embodiments, inoculation cell density is adjusted to about $10^2$ to $10^5$ CFU/ml. In some embodiments, inoculation cell density is adjusted to about $10^1$ to $10^4$ CFU/ml. In some embodiments, inoculation cell density is adjusted to about $10^0$ to $10^3$ CFU/ml. In some embodiments, inoculation cell density is adjusted to about $10^6$ to $10^8$ CFU/ml. In some embodiments, inoculation cell density is adjusted to about $10^4$ to $10^6$ CFU/ml. In some embodiments, inoculation cell density is adjusted to about $10^2$ to $10^4$ CFU/ml. In some embodiments inoculation cell density is adjusted to about $10^0$ to $10^2$ CFU/ml. In some embodiments, inoculation cell density is adjusted to $10^1$ CFU/ml. In some embodiments, inoculation cell density is adjusted to $10^2$ CFU/ml. In some embodiments, inoculation cell density is adjusted to $10^3$ CFU/ml. In some embodiments, inoculation cell density is adjusted to $10^4$ CFU/ml. In some embodiments, inoculation cell density is adjusted to $10^5$ CFU/ml. In some embodiments, inoculation cell density is adjusted to $10^6$ CFU/ml. In some embodiments, inoculation cell density is adjusted to $10^7$ CFU/ml. In some embodiments, inoculation cell density is adjusted to $10^8$ CFU/ml.

Alginate bead formation was realized by dropping the solution into a $CaCl_2$ solution bath using a vibrating nozzle. After washing to remove remaining $CaCl_2$ solution, beads were transferred to a fermenter-like system for the in-bead cultivation which may be described as a fluidized bed reactor. Growth rates and maximal cell counts resembled those from planktonic cultures, but could be slightly higher. After 24 to 72 h of cultivation, the beads were washed again. Washed beads may, optionally, be, treated with solutions containing osmoprotective compounds. The last step involved drying under ambient temperatures in appropriate drying devices (including, but not limited to a static bed in a drying chamber or drum dryer) for 24-30 hours.

Depending on the microorganism and the applied protocol, the cell density in the final product ranged from $10^9$ to $10^{12}$ CFU/g dry weight. Methods described herein enhance the ability of the formulated (stabilized) microbial cells to outlast desiccation and starvation for the time of storage and application. The inventors made the novel and unexpected discovery that that the combination of reduced inoculation density and subsequent in-bead cultivation is critical for final stability and long shelf life of the beads. In contrast to planktonic fermentation approaches, cells produced by the methods described herein are forced to multiply as colonies within the polymeric bead. Thereby, the cells produced by the methods described herein form biofilm-like structures including the generation of matrices made of extracellular polymeric substances. In fact, forming of and living in biofilms is the typical lifestyle of microorganisms in nature. Naturally, in biofilms embedded microorganisms survive adverse conditions due to the protective properties of the biofilm matrix. In one aspect of the invention, the genetic potential of any microorganism to form protective biofilms is artificially induced through a surprising combination of reduced inoculation density and in-bead cultivation, resulting in long-term improved survivability. Methods described herein are also suitable for cost-effective multi-strain fermentation. In some embodiments, only pre-culturing is performed in individual reactors, whereas the main cultivation is conducted in one single device. Moreover, the post-cultivation steps are simplified by processing only one preparation.

Example 2

Characterization of Stability of Compositions Produced Using BFC Technology

A series of experiments were performed to show the contribution of steps in the BFC technology. *Stenotrophomonas rhizophila* SPA-P69 (SPA-P69) was prepared using the following default parameters: SPA-P69 was grown in 0.5× Nutrient Broth II (SIFIN, Germany), and suspended in 1.5% sodium alginate solution to obtain a pre-culture cell density of $10^6$ CFU/ml. The composition of 0.5× Nutrient Broth II is 1.75 g/l casein peptone, 1.25 g/l meat peptone, 1.25 g/l gelatin peptone, 0.75 g/L yeast extract, and 2.5 g/l sodium chloride. Alginate beads were formed by dropping the solution into 150 mM $CaCl_2$, using a vibrating nozzle having nozzle diameter of 100 μm. The newly formed beads were washed to remove excess $CaCl_2$, and beads were transferred to a fluidized bed reactor, for secondary in-bead cultivation of encapsulated microorganisms at 22° C. for 48 hours. After cultivation the beads were washed before drying at ambient temperature in a static bed in a drying chamber for 24-30 hours. For these experiments these default parameters were modulated as described in the following table, and the viability of the encapsulated strains prepared using these experimental parameters were compared after various lengths of time in storage.

In a first experiment, the effect of the time spent in secondary cultivation was assayed. SPA-P69 was formulated by the BFC technology methodology described above except that the in-bead cultivation times were varied between samples.

Figure 14:
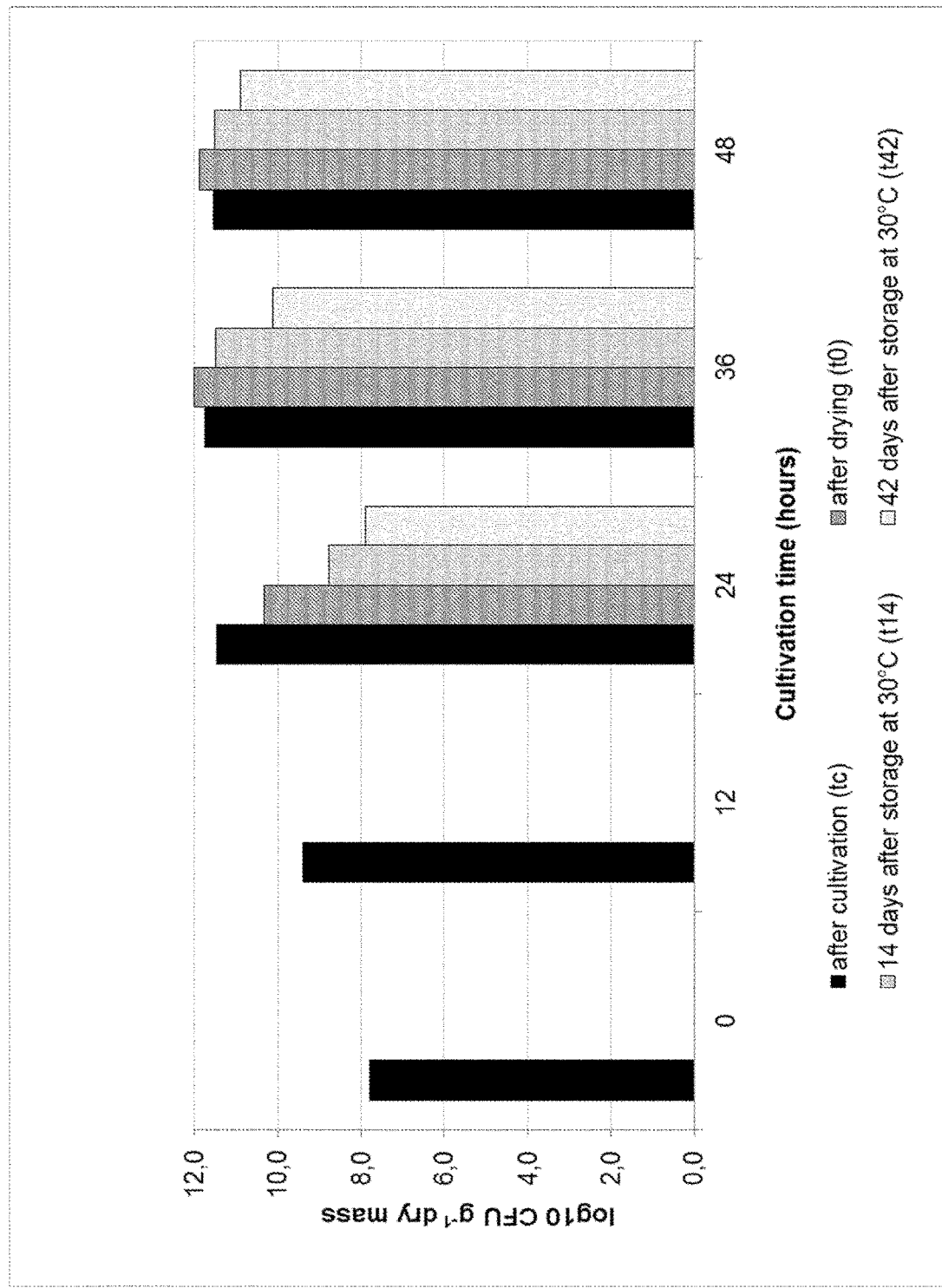
FIG. 14 Viability of *Stenotrophomonas rhizophila* SPA-P69 when formulated by the BFC technology using differing cultivation times of 0 hours, 12 hours, 24 hours, 36 hours and 48 hours, was assayed immediately after the cultivation step (tc), after the drying step (t0), 14 days after storage at 30° C., and 42 days after storage at 30° C. Encapsulated *S. rhizophila* SPA-P69 that was not prepared with a secondary cultivation step was not detectable (n.d.) after the drying step, nor at 14 or 42 days. Similarly, encapsulated *S. rhizophila* SPA-P69 that was prepared with a secondary cultivation step of 12 hours was not detectable (n.d.) after the drying step, nor at 14 or 42 days. Encapsulated *S. rhizophila* SPA-P69 that was prepared with a secondary cultivation step of 24 hours resulted in a 3.57 log reduction in CFU/g dry biomass after 42 days of storage at 30° C. relative to the CFU/g dry biomass recorded immediately after cultivation. Encapsulated *S. rhizophila* SPA-P69 that was prepared with a secondary cultivation step of 36 hours resulted in a 1.61 log reduction in CFU/g dry biomass after 42 days of storage at 30° C. relative to the CFU/g dry biomass recorded immediately after cultivation. Encapsulated *S. rhizophila* SPA-P69 that was prepared with a secondary cultivation step of 48 hours resulted in a 0.65 log reduction in CFU/g, dry biomass after 42 days of storage at 30° C. relative to the CFU/g dry biomass recorded immediately after cultivation.
Figure 15:
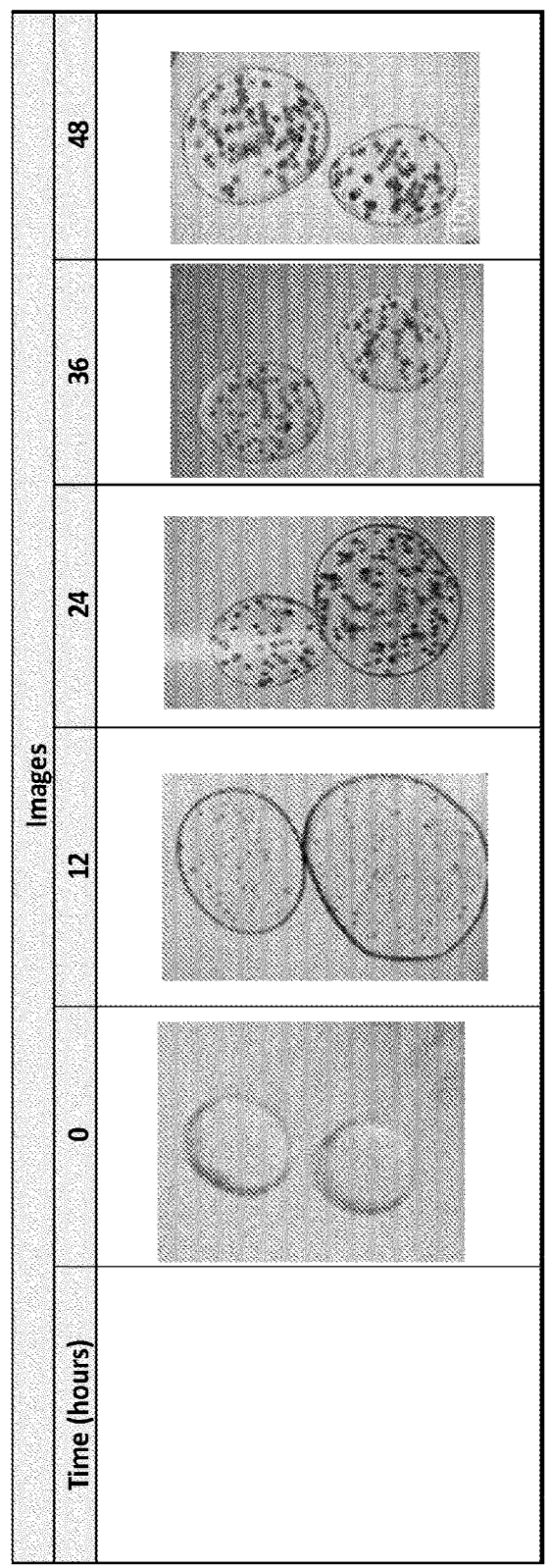
FIG. 15 Morphology of BFC encapsulated *Stenotrophomonas rhizophila* SPA-P69 before any secondary cultivation step (time hours 0), and after 12 hours of secondary cultivation, 24 hours of secondary cultivation, 36 hours of secondary cultivation, and 48 hours of secondary cultivation. The colony morphology becomes more distinct (well separated from other colonies) and dark with increasing time spent in secondary cultivation. All beads pictured were produced using an alginate concentration of 1.5%, $CaCl_2$ concentration of 150 mM, nozzle diameter of 100 μm, pre-culture inoculation density of $10^6$ CFU/ml, the strain was grown in 0.5× Nutrient Broth II (SIFIN, Germany) and cultivated at 22° C.

Encapsulated samples of SPA-P69 were subjected to in-bead cultivation of 0 hours, 12 hours, 24 hours, 36 hours and 48 hours and CFU/g dry mass was assayed immediately after the cultivation step (tc), after the drying step (t0), 14 days after storage at 30° C., or 42 days after storage at 30° C. Longer periods of in-bead cultivation resulted in increased survival of cells, this was especially noticeable when comparing samples that were stored for 42 days at 30° C. Encapsulated *S. rhizophila* SPA-P69 that was prepared with an in-bead cultivation step of 48 hours resulted in a 0.65 log reduction in CFU/g dry biomass after 42 days of storage at 30° C. relative to the CFU per g dry biomass recorded immediately after cultivation. It is also noteworthy that samples that underwent in-bead cultivation of 36 or more hours showed enhanced survival of *S. rhizophila* SPA-P69 in samples that had been dried relative to samples assayed immediately before the drying step. Results are shown in Table 2 and FIG. 14, images of exemplary beads are shown in FIG. 15.

TABLE 2

Effect of cultivation time on cell counts before, after drying and 42 days after storage at 30° C.

| Hours in-bead cultivation | After in-bead cultivation (tc) CFU/g dry mass wet beads | After drying (t0) | | After 14 days storage at 30° C. (t14) | | | After 42 days storage at 30° C. (t42) | | |
|---|---|---|---|---|---|---|---|---|---|
| | | CFU/g dry mass dried beads | Δ log10 CFU/g dry mass (t0 − tc) | CFU/g dry mass dried beads | Δ log10 CFU/g dry mass (t14 − tc) | % Δ log10 CFU/g dry mass (t14 − tc) | CFU/g dry mass dried beads | Δ log10 CFU/g dry mass (t42 − tc) | % Δ log10 CFU/g dry mass (t42 − tc) |
| 0 | 7.79 | 0.00 | −7.79 | 0.00 | 0.00 | 0.00 | 0.00 | 0.00 | 0.00 |
| 12 | 9.40 | 0.00 | −9.40 | 0.00 | 0.00 | 0.00 | 0.00 | 0.00 | 0.00 |
| 24 | 11.46 | 10.31 | −1.15 | 8.78 | −2.68 | −25.98 | 7.90 | −3.57 | −31.12 |
| 36 | 11.73 | 12.00 | 0.27 | 11.48 | −0.26 | −2.14 | 10.13 | −1.61 | −13.71 |
| 48 | 11.53 | 11.88 | 0.35 | 11.52 | −0.01 | −0.09 | 10.88 | −0.65 | −5.62 |

TABLE 1

Default and varied parameters and conditions

| | |
|---|---|
| Strain | *Stenotrophomonas rhizophila* SPA-P69 |
| Alginate concentration | 1.5% (default) |
| $CaCl_2$ concentration | 150 mM (default) |
| Nozzle diameter | 100 μm (default) |
| | 75 μm |
| Inoculation density | 1 × $10^5$ CFU/ml |
| | 1 × $10^6$ CFU/ml (default) |
| | 1 × $10^7$ CFU/ml |
| | 1 × $10^8$ CFU/ml |
| Cultivation time | 12 h |
| | 24 h |
| | 36 h |
| | 48 h (default) |
| Cultivation medium | Nutrient broth II (default) |
| Cultivation temperature | 22° C. (default) |

Figure 16:
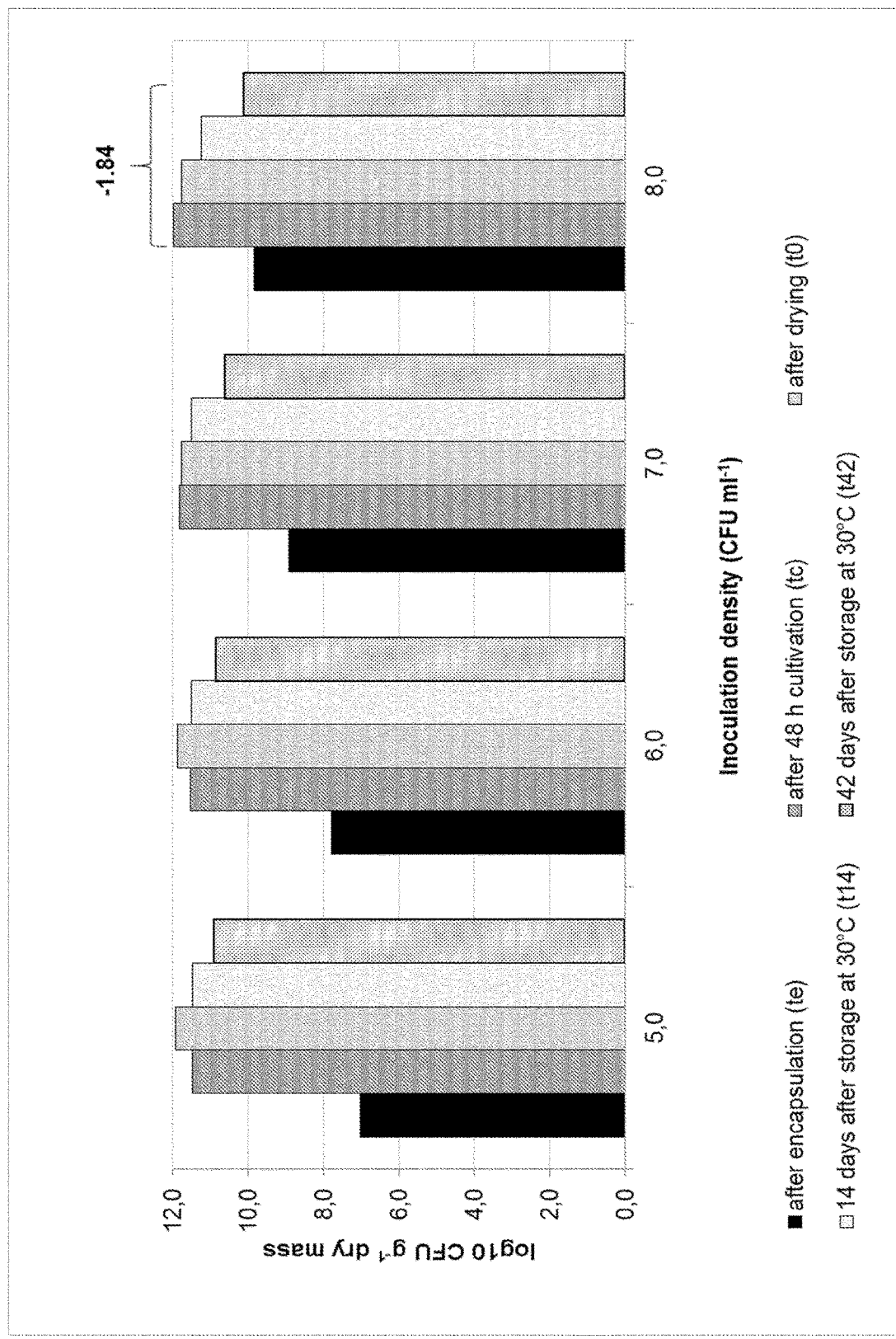
FIG. 16 Viability of *Stenotrophomonas rhizophila* SPA-P69 when formulated by the BFC technology using differing pre-in-bead culture inoculation densities ($10^5$ CFU/ml, $10^6$ CFU/ml, $10^7$ CFL/ml) after encapsulation but before secondary cultivation (te), immediately after the 48 hour secondary cultivation step (tc), after the drying step (t0), after 14 days of storage at 30° C. (t14), and after 42 days of storage at 30° C. (t42). The lower inoculation densities resulted in smaller log losses of CFU/g dry mass after storage relative to CFU/g dry mass detected immediately after the cultivation step. All beads sampled were produced using an alginate concentration of 1.5%, $CaCl_2$ concentration of 150 mM, nozzle diameter of 100 µm, pre-culture inoculation density of $10^6$ CFU/ml, the strain was grown in 0.5× Nutrient Broth II (SIFIN, Germany) and cultivated at 22° C. All beads sampled except for those labeled "te" underwent a 48 hour in-bead cultivation step.
Figure 17:
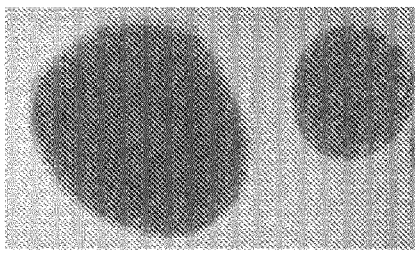
FIG. 17 Morphology of BFC encapsulated *Stenotrephomonas rhizophila* [1]SP A-P69 prepared using differing pre-culture inoculation densities ($10^5$ CFU/ml, $10^6$ CFU/ml, $10^7$ CFU/ml) was assessed after 48 hours of in-bead cultivation. Lower pre-culture inoculation densities produce distinct (well separated from other colonies) and dense colonies. All beads pictured were produced using an alginate concentration of 1.5%, $CaCl_2$ concentration of 150 mM, nozzle diameter of 100 µm, the strain was grown in 0.5× Nutrient Broth II (SIFIN, Germany) and cultivated at 22° C. in-bead for 48 hours.

In a second experiment, the effect of pre-cultivation inoculation density was assayed. SPA-P69 was formulated by the BFC technology methodology using varying inoculation densities ($10^5$ CFU/mL, $10^6$ CFU/mL, $10^7$ CFU/mL). CFU/g dry mass was assayed after encapsulation but before in-bead cultivation (te), immediately after the 48 hour in-bead cultivation step (tc), after the drying step (t0), after 14 days of storage at 30° C. (t14), and after 42 days of storage at 30° C. (t42). The lower inoculation densities resulted in smaller log losses of CFU/g dry mass after storage relative to CFU/g dry mass detected immediately after the in-bead cultivation step. Results are shown in Table 3 and FIG. 16, images of exemplary beads are shown in FIG. 17. Table 4 describes characteristics of colonies formed within the beads prepared using the BFC technology methodology with differing inoculation densities.

TABLE 3

Effect of pre-cultivation inoculation density on cell counts before, after drying and 42 days after storage at 30° C.

| Inoculation density | After encapsulation (te) | After 48 hour in-bead cultivation (tc) | | After drying (t0) | | After 14 days storage at 30° C. (t14) | | | After 42 days storage at 30° C. (t42) | | |
|---|---|---|---|---|---|---|---|---|---|---|---|
| | CFU/g dry mass wet beads | CFU/g dry mass wet beads | Δ log10 CFU/g dry mass (tc − te) | CFU/g dry mass dried beads | Δ log10 CFU/g dry mass (t0 − tc) | CFU/g dry mass dried beads | Δ log10 CFU/g dry mass (t14 − tc) | % Δ log10 CFU/g dry mass (t14 − tc) | CFU/g dry mass dried beads | Δ log10 CFU/g dry mass (t42 − tc) | % Δ log10 CFU/g dry mass (t42 − tc) |
| $10^5$ | 7.03 | 11.47 | 4.45 | 11.92 | 0.45 | 11.49 | 0.02 | 0.15 | 10.92 | −0.55 | −4.82 |
| $10^6$ | 7.79 | 11.53 | 3.74 | 11.88 | 0.35 | 11.52 | −0.01 | −0.09 | 10.88 | −0.65 | −5.62 |
| $10^7$ | 8.84 | 11.83 | 2.89 | 11.78 | −0.05 | 11.50 | −0.33 | −2.84 | 10.63 | −1.20 | −10.16 |
| $10^8$ | 9.85 | 11.97 | 2.12 | 11.76 | −0.21 | 11.24 | −0.74 | −6.25 | 10.13 | −1.84 | −15.41 |

TABLE 4

Characteristics of colonies formed within the beads prepared using the BFC technology methodology with differing inoculation densities

| | Inoculation density | | | |
|---|---|---|---|---|
| | 1.0E+5 | 1.0E+6 | 1.0E+7 | 1.0E+8 |
| Number of colonies/bead | 12.5 | 125 | 1250 | 12500 |
| Colony diameter (μm) | 16.42 | 9.33 | 5.58 | n.d. |
| Colony volume (μm^3) | 1.89E+4 | 3.37E+3 | 1.29E+3 | n.d. |
| CFU/colony | 1.14E+05 | 2.02E+4 | 7.74E+3 | n.d. |
| CFU/bead | 1.42E+06 | 2.53E+6 | 9.68E+6 | n.d. |

Example 3

Metabolic Profiling of Microorganisms Formulated by Bacterial and Fungal Conservation (BFC) Technology Using High Resolution Mass Spectrometry Preparation of Strains Using BFC and Reference Methods

*Stenotrophomonas rhizophila* SPA-P69, *Sphingomonas sanguinis*, *Pseudomonas brassicacearum* L 13, and *Serratia plymuthica* 3Re were each individually formulated using the BFC methodology. To generate reference alginate encapsulated planktonically grown cells ("Alginate Planktonic"), cells in liquid culture were pelleted and resuspended in 1/10 the initial volume using 0.9% NaCl. The 10 fold concentrated cell suspension was mixed with alginate solution such that cell densities in the resulting alginate beads were similar to densities obtained after in-bead cultivation. Immediately following bead formation, Alginate Planktonic beads were air dried and stored at 30° C. Reference alginate encapsulated *Stenotrophomonas rhizophila* SPA-P69, *Pseudomonas brassicacearum* L 13, and *Serratia plymuthica* 3Re were also prepared using the method of Bashan (1986).

Preparation of Samples

For metabolite analyses, about 100 mg cell mass for each sample and replicate (3 per microbe/method) were collected. Cell material from planktonically grown bacteria were obtained by pelleting 1.9 ml of a liquid culture in 2 ml tubes at 13,500×g for 15 min at 4° C. and discarding the supernatant. Samples from bacteria immobilized in alginate beads were prepared by dissolving 200 mg of dry beads in 40 ml 50 mM. $Na_3C_6H_5O_7$ in 50 ml tubes using an orbital shaker for 3 hours at room temperature. The bacterial pellet was obtained by two centrifugation steps. The first centrifugation step was done at 9,000×g for 20 min at 10° C. After discarding the supernatant, the remaining pellet was re-suspended in 1.0 ml 50 mM $Na_3C_6H_5O_7$ followed by an additional centrifugation step at 13,500×g for 15 min at 4° C. and removal of the supernatant. The mass of alginate pellets were weighed.

For disrupting bacterial cells, the pellet was re-suspended in 1 ml −70° C. cold methanol, transferred to 2 ml screw-capped tubes containing 250 mg glass beads with a diameter of 0.25-0.5 mm and three glass beads with a diameter of 3 mm, and treated using the FastPrep-24 Instrument (MPBiomedicals, Illkrich, France) for 2×30 s at speed level 4 (lowest). Finally, to remove cell debris, the suspension was centrifuged at 13,500 for 15 min at 4° C. 500 μl of the supernatant was collected and stored at −70° C. until analysis. For preparing sample blanks of the cultivation medium (NBII), aliquots of 100 μl nutrient broth II were mixed with 1 ml methanol. Sample blanks for alginate beads derived samples were obtained by dissolving 2 g of wet, sterile alginate beads in 40 ml $Na_3C_6H_5O_7$ (50 mM) and mixing 100 μl of the solution with 1 ml methanol.

The characteristics of the samples are additionally described in Table 5.

TABLE 5

Average characteristics of samples prepared for metabolite profiling.

| | *Stenotrophomonas rhizophila* SPA-P69 | | | | *Sphingomonas sanguinis* | | |
|---|---|---|---|---|---|---|---|
| | BFC (in-bead cultivation) | Planktonic | Alginate encapsulated planktonic | Bashan | BFC (in-bead cultivation) | Planktonic | Alginate encapsulated planktonic |
| Cell count/ml (g dry beads) | 1.78E+11 | 2.96E+09 | 6.78E+10 | 9.11E+10 | 8.43E+09 | 2.65E+09 | 7.01E+09 |
| Volume ml (mass g) of sample | 2.00E−01 | 1.50E+00 | 2.00E−01 | 2.00E−01 | 2.00E−01 | 1.50E+00 | 2.00E−01 |

TABLE 5-continued

Average characteristics of samples prepared for metabolite profiling.

| | Stenotrophomonas rhizophila SPA-P69 | | | | Sphingomonas sanguinis | | |
| --- | --- | --- | --- | --- | --- | --- | --- |
| | BFC (in-bead cultivation) | Planktonic | Alginate encapsulated planktonic | Bashan | BFC (in-bead cultivation) | Planktonic | Alginate encapsulated planktonic |
| Weight of pellet (mg) | 1.07E+02 | 9.78E+01 | 1.03E+02 | 1.02E+02 | 1.02E+02 | 9.61E+01 | 1.00E+02 |
| Calculated CFU/ LC-MS Sample | 3.57E+10 | 4.45E+09 | 1.36E+10 | 1.82E+10 | 1.69E+09 | 3.97E+09 | 1.40E+09 |

Metabolic Profiling Using High Resolution Mass Spectrometry

For metabolite analysis, a Thermofisher, HPLC and Orbitrap (Q-Exactive) HPLC-MS-System was used with the following specifications: Column was an Atlantis dC18, 3 µm, 2, 1×100 mm; Flow was set at 0.3 ml/min; Gradient was 10% B (2 min)-50% B (5 min)-80% (15 min)-10% B (5 min), with a total run time of 40 min; Mobile Phase A was 0.1% Formic Acid/H2O$_{dd}$; B: 0.1% Formic Acid/Acetonitril.

Specific mass spec parameters were as follows: Voltage. 3100; Capillary Temperature: 330; Positive, Negative Mode extra; Resolution: 70.000, AGC target: 1 e6, Maximum IT: 200 ms, Scan Range: 100 to 1500 m/z; MS2-Parameter: Resolution: 17.500.

Mass spec general settings were as follows: Precursor Selection: Use MS(n-1) Precursor; Use New Precursor Reevaluation: True; Use Isotope Pattern in Precursor Reevaluation: True; Store Chromatograms: False.

Spectrum Properties Filter settings were as follows: Lower RT Limit: 0; Upper RT Limit: 0; First Scan: 0; Last Scan: 0; —Ignore Specified Scans: (not specified); Lowest Charge State: 0; Highest Charge State: 0; Min. Precursor Mass: 100 Da; Max. Precursor Mass: 5000 Da; Total Intensity Threshold: 0; Minimum Peak Count: 1.

Scan Event Filter settings were as follows: Mass Analyzer: (not specified);—MS Order: Any; Activation Type: (not specified); Min. Collision Energy: 0; Max.

Collision Energy: 1000; Scan Type: Any; Polarity Mode: (not specified).

Peak filter settings were as follows: S/N Threshold (FT-only): 1.5.

Replacements for Unrecognized Properties settings were as follows: Unrecognized Charge Replacements: 1; Unrecognized Mass Analyzer Replacements: ITMS; Unrecognized MS Order Replacements: MS2; Unrecognized Activation Type Replacements: CID; Unrecognized Polarity Replacements: +; Unrecognized MS Resolution®200 Replacements: 60000; Unrecognized MSn Resolution®200 Replacements: 30000.

HPLC mass spec data analysis was performed using Compound Discoverer version 2.1.0,398 (Thermofisher) and an untargeted metabolomics workflow to find and identify the differences between samples. The workflow data analysis included retention time alignment, unknown compound detection, and compound grouping across all samples, predicted elemental compositions for all compounds, filled gaps across all samples, and hid chemical background (using Blank samples).

For grouping unknown compounds, Compound Consolidation settings were as follows: Mass Tolerance: 5 ppm, RT Tolerance [min]: 0.05. Fragment Data Selection used the following Preferred Ions: [M+H]+1; [M−H]−1. To fill gaps, the following General Settings were used: Mass Tolerance: 5 ppm, S/N Threshold: 1.5, Use Real Peak Detection: True. To normalize areas, QC-based Area Correction settings were as follows: Regression Model: Linear, Min, QC Coverage [%]: 50, Max. QC Area RSD [%]: 30, Max. # Files Between QC Files: 20. Area Normalization settings were as follows: Normalization Type: None, Exclude Blanks: True.

For unknown compound detection mass tolerance was set at 5 ppm, intensity tolerance at 30%, S/N threshold of 3, min. peak intensity of 1000000, ions:

[2M+ACN+H]+1, [2M+ACN+Na]+1, [2M+FA−H]−1, [2M+H]+1, [2M+Na]+1, [2M+NH4]+1, [2M−H]−1, [2M−H+HAc]−1, [M+2H]+2, [M+3H]+3, [M+ACN+2H]+2, [M+ACN+H]+1, [M+ACN+Na]+1, [M+Cl]−1, [M+FA−H]−1, [M+H]+1, [M+H+K]+2, [M+H+Na]+2, [M+H+NH4]+2, [M+H−H2O]+1, [M+H−NH3]+1, [M+K]+1, [M+Na]+1, [M+NH4]+1, [M−2H]−2, [M−2H+K]−1, [M−H]−1, [M−H+HAc]−1, [M−H−H2O]−1, Base Ions: [M+H]+1; [M−H]−1, Min. Element Counts: C H, Max. Element Counts: C90 H190 Cl4 K2 N10 Na2 O15 P3 S5.

For peak detection, -the following settings were used: Filter Peaks: True, Max. Peak Width [min]: 0.5, Remove Singlets: True, Min, # Scans per Peak: 5, Min. # isotopes: 1. QC-based area correction and area normalization settings were as follow: QC-based Area Correction: Regression Model: Linear, Min. QC Coverage [%]: 50, Max. QC Area RSD [%]: 30, Max. # Files Between QC Files: 20; Area Normalization:

Normalization Type: None, Exclude Blanks: True. Composition prediction settings were as follows: Mass Tolerance: 5 ppm, Min. Element Counts: C H, Max. Element Counts: C90 H190 C14 N10 O18 P3 S5, Min. RDBE: −1, Max. RDBE: 40, Min. H/C: 0.1, Max. H/C: 4, Max. # Candidates: 10, Max. # Internal Candidates: 200. Fragment matching settings were as follows: Use Fragments Matching: True, Mass Tolerance: 5 mmu, S/N Threshold: 3.

Compounds were identified using mzCloud (ddMS2) and ChemSpider (formula or exact mass). mzCloud search settings were as follows: Compound Classes: All, Match Ion Activation Type: False, Match Ion Activation Energy: Match with Tolerance, Ion Activation Energy Tolerance: 20, Apply Intensity Threshold: True, Precursor Mass Tolerance: 10 ppm, FT Fragment Mass Tolerance: 10 ppm, IT Fragment Mass Tolerance: 0.4 Da, Identity Search: HighChem HighRes, Similarity Search: Similarity Forward, Library: Reference, Post Processing: Recalibrated, Match Factor Threshold: 50, Max. # Results: 10. Pattern matching settings were as follows: Intensity Tolerance [%]: 30, Intensity Threshold [%]: 0.1, S/N Threshold: 3, Min.

Spectral Fit [%]: 30, Min. Pattern Cov. [%]:90, Use Dynamic Recalibration: True.

ChemSpider used the following data sources: BioCyc, *E. coli* Metabolome Database, Human Metabolome Database, KEGG, MeSH, NIST Chemistry WebBook Spectra, PubChem, and the Yeast Metabolome Database.

Similarity searches were also performed for all compounds with ddMS2 data using mzCloud. Compounds were mapped to biological pathways using KEGG database. Map to KEGG pathway used the following settings: 1. By Mass Search Settings: Mass Tolerance: 5 ppm; 2. By Formula Search Settings: Max. # of Predicted Compositions to be searched per Compound: 3, and 3. Display Settings: Max. # Pathways in 'Pathways' column: 20.

QC-based batch normalization was applied when QC samples were available. Workflow also included differential analysis calculation (t-test or ANOVA), p-value determination, adjusted p-value determination, ratios, fold change, and CV.

Using ThermoFisher Compound Discoverer, comma-separated variable (CSV) files representing the Input Files Table and Expected Features Table were exported as described in the Thermo Compound Discoverer User Guide (available at thermofisher.com). All downstream processing and analysis was performed in the R statistical language R, version 3.5.1 (R Core Team, 2016. R: A language and environment for statistical computing. R Foundation for Statistical Computing, Vienna, Austria. R-project.org/). Unless stated otherwise, all analyses were performed identically but separately for positive and negative ion datasets. Peak groups were constructed using the XCMS function do_groupChromPeaks_nearest with default parameters (Smith et al. (2006). *XCMS: Processing mass spectrometry data for metabolite profiling using Nonlinear peak alignment, matching, and identification.*

Analytical Chemistry, 78:779-787). Within each sample, intensities of peaks having identical m/z and retention time were summed. All sample datasets were aggregated into a single matrix, with a NA indicator representing the absence of detection of a particular peak in a particular sample. To increase dataset density, metabolites represented by NA in over half of the samples were removed. Remaining NA values were replaced with a minimum intensity value, defined as one-half of the smallest, nonzero intensity of the dataset. To normalize intensity levels across the samples, quantile normalization was performed using the "normalize.quantiles" function in the preprocessCore package Bolstad B (2018). preprocessCore: A collection of preprocessing functions. R package version 1.42.0, available at github.com/bmbolstad/preprocessCore). Normalized intensities were log-2 transformed for subsequent statistical analysis.

To reduce unnecessary multiplicity of statistical hypothesis testing, nonspecific filtering was performed using genefilter [Gentleman2018] to eliminate metabolites with a coefficient of variance less than 0.03 or an interquantile range of less than 0.5. Statistical t-testing was performed with the limma function lmFit (Ritchie et al. (2015). "limma powers differential expression analyses for RNA-sequencing and microarray studies." *Nucleic Acids Research*, 43(7), e47.), using an empirical Bayesian estimate for variance via the eBayes function, and using the topTable function to obtain a Benjamini and Hochberg p-value adjustment. To project metabolites onto known metabolic pathways and compound names, the mummichog algorithm (Li et al. Predicting Network Activity from High Throughput Metabolomics. Ouzounis C A, ed. *PLoS Computational Biology.* 2013; 9(7):e1003123) was used via the implementation in MetaboAnalystR (Chong & Xia (2018) MetaboAnalystR: an R package for flexible and reproducible analysis of metabolomics data. *Bioinformatics.* 2018 Jun. 28). The InitDataObjects was called with analysis type set to "mummichog", followed by UpdateMummichogParameters with instrumentOpt set to "0.1", ion polarity set to positive or negative, and pvalCutoff set to 1.0E-6. Finally, the PerformMummichog function was called with an appropriate prokaryote model, along with "fisher" and "gamma" parameters for enrichOpt and pvalOpt, respectively. Compound identifiers were mapped to the corresponding descriptive KEGG names (Kanehisa & Goto (2000) KEGG: kyoto encyclopedia of genes and genomes. *Nucleic Acids Res.* 28(1):27-30). The log fold change was adjusted to reflect the relative CFU/LC-MS sample.

Compounds increased in RFC formulated *Sphingomonas sanguinis* and *Stenotrophomonas rhizophila* SPA-P69 relative to reference compositions are shown in Table 6A. Compounds increased in BFC formulated *Sphingomonas sanguinis* relative to reference composition Alginate Planktonic are shown in Table 6B. EPS refers to an extracellular polymeric substance. Exemplary compounds should be understood to include related compounds such as oxidized and reduced forms and derivatives.

TABLE 6A

Compounds increased in BFC formulated *Sphingomonas sanguinis* and *Stenotrophomonas rhizophila* SPA-P69 relative to reference compositions

| Classes or Functions | Exemplary Compound(s) | Range of titer-adjusted fold-change relative to reference compositions | *Sphingomonas sanguinis* Titer-adjusted fold-change of BFC relative to reference composition Alginate Planktonic | *Stenotrophomonas rhizophila* SPA-P69 Titer-adjusted fold-change of BFC relative to reference composition Alginate Planktonic | Titer-adjusted fold-change of BFC relative to reference composition Bashan |
|---|---|---|---|---|---|
| Other | naphthazarin | 13.8-485.3 | 485.33 | 13.83 | 75.04 |
| Vitamin/Redox | NAD+/NADH | 1.25-4.0 | 3.13 | 3.73 | 3.98 |
| | Thiamine | 2.3-143.5 | 143.48 | 9.59 | 2.26 |
| | Adenine | 1.1-15.9 | 7.46 | 15.95 | 1.07 |
| AA, protein, | tryptophan | 1.7-13.9 | 13.89 | 2.77 | 3.79 |
| EPS | phenylalanine | 1.3-4.4 | 4.40 | 1.28 | 1.58 |
| AA, non-protein | homocysteine | 3.7-16.1 | 16.09 | 6.65 | 3.69 |
| Stabilization | tryptophan | 1.7-13.9 | 13.89 | 2.77 | 3.79 |

TABLE 6A-continued

Compounds increased in BFC formulated *Sphingomonas sanguinis* and *Stenotrophomonas rhizophila* SPA-P69 relative to reference compositions

| Classes or Functions | Exemplary Compound(s) | Range of titer-adjusted fold-change relative to reference compositions | *Sphingomonas sanguinis* Titer-adjusted fold-change of BFC relative to reference composition Alginate Planktonic | *Stenotrophomonas rhizophila* SPA-P69 Titer-adjusted fold-change of BFC relative to reference composition Alginate Planktonic | *Stenotrophomonas rhizophila* SPA-P69 Titer-adjusted fold-change of BFC relative to reference composition Bashan |
|---|---|---|---|---|---|
| Pathway cycling | homocysteine | 3.7-16.1 | 16.09 | 6.65 | 3.69 |
| | erythrose 4-phosphate | 3.2-9.7 | 8.06 | 2.03 | 1.64 |
| | pyridoxine phosphate | 3.1-5.3 | 4.40 | 1.28 | 1.58 |
| | phenylalanine | 1.3-4.4 | 4.40 | 1.28 | 1.58 |

TABLE 6B

Compounds increased in BFC formulated *Sphingomonas sanguinis* relative to reference composition Alginate Planktonic

| Classes/Functions | Exemplary Compound(s) | *Sphingomonas sanguinis* Titer-adjusted fold-change of BFC relative to reference composition Alginate Planktonic |
|---|---|---|
| Other | naphthazarin | 485.33 |
| Vitamin/Redox | Thiamine | 143.48 |
| | Nicotinamide | 8.12 |
| | Adenine | 7.46 |
| | NAD+/NADH | 3.13 |
| Stabilization | glutamic acid/glutamate | 55.44 |
| | tryptophan | 13.89 |
| | spermidine | 6.07 |
| | Pyocyanin | 1.55 |
| Pathway cycling | homocysteine | 16.09 |
| | adenosine | 10.18 |
| | erythrose 4-phosphate | 8.06 |
| | pyridoxine phosphate | 4.40 |
| | phenylalanine | 4.40 |
| | methionine | 4.16 |
| | N-methylene-L-glutamate | 0.91 |
| Other | methylthioninium chloride | 1.82 |
| EPS | glucosamine/chitosamine | 6.58 |
| DNA/RNA, EPS | Cytosine/adenine | 8.95 |
| Antioxidant | glutathione | 97.31 |
| | citric acid | 8.21 |
| | Pyocyanin | 1.55 |
| AA, protein, EPS | glutamic acid/glutamate | 55.44 |
| | tryptophan | 13.89 |
| | tyrosine | 6.58 |
| | phenylalanine | 4.40 |
| | methionine | 4.16 |
| | lysine | 2.70 |
| | proline | 2.63 |
| AA, non-protein | homocysteine | 16.09 |

TABLE 6C

Compounds increased in BFC formulated *Stenotrophomonas rhizophila* SPA-P69 relative to reference compositions

| Classes/Functions | Exemplary Compound(s) | *Stenotrophomonas rhizophila* SPA-P69 Titer-adjusted fold-change of BFC relative to reference composition Alginate Planktonic | *Stenotrophomonas rhizophila* SPA-P69 Titer-adjusted fold-change of BFC relative to reference composition Bashan |
|---|---|---|---|
| Other | naphthazarin | 13.83 | 75.04 |
| AA, non-protein | homocysteine | 6.65 | 3.69 |
| AA, protein, EPS | tryptophan | 2.77 | 3.79 |
| | phenylalanine | 1.28 | 1.58 |

TABLE 6C-continued

Compounds increased in BFC formulated *Stenotrophomonas rhizophila* SPA-P69 relative to reference compositions

| Classes/ Functions | Exemplary Compound(s) | *Stenotrophomonas rhizophila* SPA-P69 | |
|---|---|---|---|
| | | Titer-adjusted fold-change of BFC relative to reference composition Alginate Planktonic | Titer-adjusted fold-change of BFC relative to reference composition Bashan |
| Osmolyte | Rhamnose | 1.48 | 2.38 |
| Pathway | homocysteine | 6.65 | 3.69 |
| cycling | erythrose 4-phosphate | 2.03 | 1.64 |
| | pyridoxine phosphate | 1.28 | 1.58 |
| | phenylalanine | 1.28 | 1.58 |
| Stabilization | tryptophan | 2.77 | 3.79 |
| Vitamin/Redox | NAD+/NADH | 3.73 | 3.98 |
| | Thiamine | 9.59 | 2.26 |
| | Adenine | 15.95 | 1.07 |

Example 4

Colony Characteristics within BFC Produced Beads

*Paraburkholderia caledonica* and *Enterobacter cowanii* were prepared by the BFC method using pre-culture inoculation densities of between 2E+7 and 4E+7 with differing times of in-bead cultivation, and for *Enterobacter cowanii* differing alginate percentages and nozzle diameters were used.

*Paraburkholderia caledonica* samples were prepared using an 80 µm diameter nozzle and a 2% alginate solution. In-bead cultivation was performed for 47, 138, or 168 hours. *Enterobacter cowanii* samples were prepared using 80 µm diameter nozzle and a 120 µm diameter nozzle and 2% and 3% alginate solutions. In-bead cultivation was performed for 50, 70, or 71 hours. Beads produced by the 80 µm diameter nozzle produced beads had an average diameter of 186 µm and a range of 134-235 µm when wet, and an average diameter of 78 µm and range of 50-103 µm after drying. The beads had approximately between 2 and 100 colonies per bead. The average, smallest and largest bead diameters are listed in Tables 7A and 7B. Colony diameter was measured at the widest point of the colony. Colony measurements were made in wet beds. Increasing in-bead cultivation time resulted in only moderate increases in colony diameter.

TABLE 7A

Colony size measurements of BFC encapsulated *Paraburkholderia caledonica*
*Paraburkholderia caledonica* Colony Size Measurements

| Batch | Time (hr) | Smallest colony (µm) | Average colony (µm) | Largest colony (µm) |
|---|---|---|---|---|
| 180907-80 µM-2% Alginate | 47 | 16 | 21 | 35 |
| 180907-80 µM-2% Alginate | 138 | 15 | 25 | 37 |
| 180907-80 µM-2% Alginate | 168 | 19 | 27 | 41 |
| | Avg: | 16 | 24 | 38 |

TABLE 7B

Colony size measurements of BFC encapsulated *Enterobacter cowanii*
*Enterobacter cowanii* Colony Size Measurements

| Batch | Time (hr) | Smallest colony (µm) | Average (µm) | Largest (µm) |
|---|---|---|---|---|
| 180803-175-80 µM: 2% Alginate | 50 | 21 | 32 | 40 |
| 180620-175-80 µM: 3% Alginate | 70 | 26 | 31 | 33 |
| 180619-175-120 µM: 3% Alginate | 71 | 24 | 37 | 43 |
| | Avg: | 24 | 33 | 39 |

The invention claimed is:

1. A method for improving the viability of microorganisms during storage and application, comprising the steps of:
   a) suspending one or more pre-cultures of microorganisms in polymeric substance solution,
   b) immobilizing said microorganisms by dropping the solution of step a) into multivalent ion solution thereby obtaining encapsulated microorganisms in polymeric particles,
   c) cultivating the encapsulated microorganisms in said polymeric particles for at least 12 hours in liquid media until an increase of the cell density of at least 2 to 10 log is obtained, wherein the microorganisms are in the form of multicellular aggregates within the polymeric particles, and wherein the microorganisms within the aggregates are embedded in a self-produced extracellular biogenic matrix,
   d) collecting the polymeric particles, and
   e) drying the polymeric particles.

2. The method of claim 1, wherein the collected polymeric particles comprise one or more multicellular aggregates between 14 µm and 43 µm in diameter.

3. The method of claim 1, wherein the dried polymeric particles are rehydrated and comprise one or more multicellular aggregates between 14 µm and 43 µm in diameter.

4. The method of claim 1, wherein the polymeric substance comprises a biodegradable polymer, and wherein the biodegradable polymer is selected from the group consisting of albumin, collagen, gelatin, fibrinogen, casein, fibrin, hemoglobin, transferrin, chitin, chitosan, hyaluronic acid, heparin, chondroitin, keratin sulfate, alginate, starch, dextrin, dextran, polylactic acid, polyglycolic acid, lactic acid-glycolic acid copolymer, polyhydroxybutyric acid, polycaprolactone, polyanhydride, agarose, agar, chitosan, and polyalkylcyanoacrylate.

5. The method of claim 1, wherein at least one of the polymeric particles has a diameter of less than 200 µm.

6. The method of claim 1, wherein the encapsulated microorganisms are bacterial or fungal cells.

7. The method of claim 1, wherein the encapsulated microorganisms comprise at least two microorganisms of distinct genetic origins.

8. The method of claim 7, wherein the at least two microorganisms of distinct genetic origins are from at least two types of microorganisms selected from the group consisting of archaea, protozoa, bacteria, fungi and algae.

9. The method of claim 1, wherein step c) comprises cultivating the encapsulated microorganisms in said polymeric particles for at least 24 hours.

10. The method of claim 1, wherein step c) comprises cultivating the encapsulated microorganisms at 20-30° C.

11. The method of claim 1, wherein step c) comprises cultivating the encapsulated microorganisms until an increase of at least 4 log is obtained.

* * * * *